(12) United States Patent
Onoda et al.

(10) Patent No.: US 7,857,753 B2
(45) Date of Patent: Dec. 28, 2010

(54) ENDOSCOPE SHAPE DETECTION DEVICE

(75) Inventors: Fumiyuki Onoda, Tama (JP); Hiroshi Niwa, Koganei (JP); Tomohiko Oda, Kawagoe (JP); Minoru Sato, Hino (JP); Kensuke Miyake, Hachioji (JP); Yoshitaka Miyoshi, Hachioji (JP); Kazutaka Tuji, Hachioji (JP); Chieko Aizawa, Hachioji (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 669 days.

(21) Appl. No.: 11/800,479

(22) Filed: May 4, 2007

(65) Prior Publication Data

US 2007/0219410 A1    Sep. 20, 2007

Related U.S. Application Data

(63) Continuation of application No. PCT/JP2005/020863, filed on Nov. 14, 2005.

(30) Foreign Application Priority Data

Nov. 15, 2004 (JP) ............................. 2004-331069
Mar. 14, 2005 (JP) ............................. 2005-071716
Mar. 31, 2005 (JP) ............................. 2005-104130

(51) Int. Cl.
*A61B 1/00* (2006.01)
(52) U.S. Cl. .................. 600/117; 600/118; 600/424
(58) Field of Classification Search ................ 600/101, 600/103, 117–118, 146, 162, 409, 424
See application file for complete search history.

(56) References Cited

U.S. PATENT DOCUMENTS

| 5,840,024 | A |   | 11/1998 | Taniguchi et al. |
| 5,997,473 | A | * | 12/1999 | Taniguchi et al. ............ 600/117 |
| 6,059,718 | A | * | 5/2000 | Taniguchi et al. ............ 600/117 |
| 6,432,041 | B1 |   | 8/2002 | Taniguchi et al. |
| 6,511,417 | B1 | * | 1/2003 | Taniguchi et al. ............ 600/117 |

(Continued)

FOREIGN PATENT DOCUMENTS

JP    2000-093986    4/2000

(Continued)

OTHER PUBLICATIONS

Abstract of Japanese Publication No. 2000-175862, published Jun. 27, 2000.

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A source coil drive circuit section of an endoscope shape detection device includes, an oscillator that generates a sine wave and an amplifier that amplifies the sine wave and generates (drives) an alternating magnetic field to source coils through a switch section. The switch section is configured to switch a direct current to an output of the amplifier and supply to the source coils. In the source coil drive circuit section, a direct current resistance value detection section for measuring a direct current resistance value of the source coils by voltage drop when the switch section is supplying the direct current to the source coils is provided.

27 Claims, 24 Drawing Sheets

U.S. PATENT DOCUMENTS

| | | | |
|---|---|---|---|
| 6,589,163 B2 * | 7/2003 | Aizawa et al. | 600/118 |
| 6,773,393 B1 * | 8/2004 | Taniguchi et al. | 600/117 |
| 6,773,394 B2 * | 8/2004 | Taniguchi et al. | 600/117 |
| 7,174,202 B2 * | 2/2007 | Bladen et al. | 600/424 |
| 7,195,587 B2 * | 3/2007 | Taniguchi et al. | 600/117 |
| 2002/0169361 A1 * | 11/2002 | Taniguchi et al. | 600/117 |
| 2003/0055317 A1 * | 3/2003 | Taniguchi et al. | 600/117 |
| 2003/0199756 A1 * | 10/2003 | Kawashima | 600/424 |
| 2004/0116775 A1 | 6/2004 | Taniguchi et al. | |
| 2005/0171427 A1 * | 8/2005 | Nevo et al. | 600/424 |

FOREIGN PATENT DOCUMENTS

| | | |
|---|---|---|
| JP | 2001-231743 | 8/2001 |
| JP | 3290153 | 3/2002 |
| JP | 2003-245242 | 9/2003 |
| JP | 2003-245243 | 9/2003 |
| JP | 2003245243 A * | 9/2003 |
| JP | 2003-290129 | 10/2003 |

OTHER PUBLICATIONS

Extended Supplementary European Search Report dated Aug. 5, 2010.

* cited by examiner

ENDOSCOPE SHAPE DETECTION DEVICE

CROSS REFERENCE TO RELATED APPLICATION

This application is a continuation application of PCT/JP2005/020863 filed on Nov. 14, 2005 and claims the benefit of Japanese Applications No. 2004-331069 filed in Japan on Nov. 15, 2004, No. 2005-071716 filed in Japan on Mar. 14, 2005, and No. 2005-104130 filed in Japan on Mar. 31, 2005, the entire contents of each of which are incorporated herein by their reference.

BACKGROUND OF THE INVENTION

1. Field of the Invention

The present invention relates to an endoscope shape detection device for detecting and displaying an insertion shape of an endoscope or the like using magnetic field generation elements and magnetic field detection elements.

2. Description of the Related Art

In recent years, endoscope shape detection devices that detect, for example, a shape of an endoscope inserted into inside of a body or the like using magnetic field generation elements and magnetic field detection elements, and display the shape with display means have been used.

For example, Japanese Unexamined Patent Application Publication No. 2003-245243 discloses a device that detects an endoscope shape using magnetic fields and displays the detected endoscope shape. The device drives a plurality of magnetic field generation elements disposed at predetermined intervals in an insertion part of an endoscope to be inserted into inside of a body, and generates magnetic fields around the elements. Then, the device, using magnetic field detection elements disposed outside the body, based on the generated magnetic fields, detects three-dimensional positions of each of the magnetic field generation elements. According to the three-dimensional position information of the each of the detected magnetic field generation elements, curves that sequentially connect the each of the magnetic field generation elements are generated, and a three-dimensional image of the modeled insertion part is displayed with display means.

Operators or the like can observe the image and realize a position of a distal end part of the insertion part being inserted into inside of the body, an insertion shape, or the like. Accordingly, it is possible to smoothly perform the insertion operation to a target part, or the like.

SUMMARY OF THE INVENTION

An endoscope shape detection device comprising:

a detection section having either one of a plurality of magnetic field generation elements and a plurality of magnetic field detection elements disposed in an insertion part of an endoscope to be inserted into a subject and the other elements disposed outside the subject, and, detecting each position of the one elements disposed in the insertion part using positions of the other elements as a reference;

a shape estimation section for estimating a shape of the endoscope insertion part based on the detection result of the detection section;

a property value detection section for detecting an electric property value of the magnetic field generation elements;

a storage section for storing a reference value of the electric property value; and a state detection section for detecting a state of the magnetic field generation elements based on the electric property value of the magnetic field generation elements detected by the property value detection section and the reference value.

DETAILED DESCRIPTION OF THE PREFERRED EMBODIMENT(S)

Hereinafter, embodiments of the present invention will be described with reference to the drawings.

First Embodiment

Figure 1:
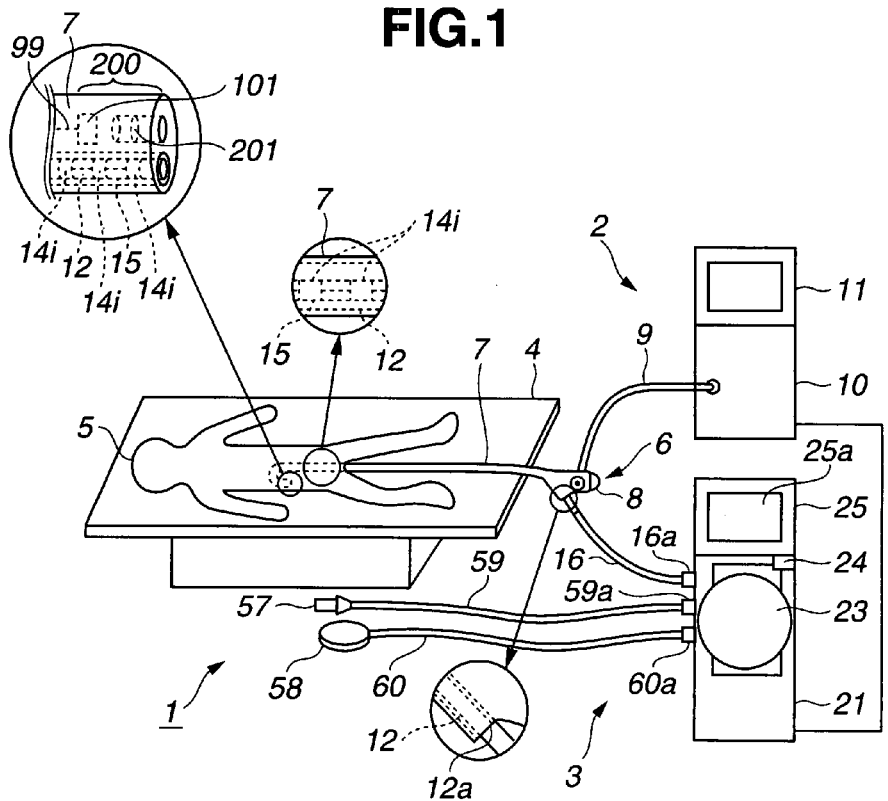
FIG. 1 is a configuration view illustrating a configuration of an endoscope system according to a first embodiment of the present invention.
Figure 2:
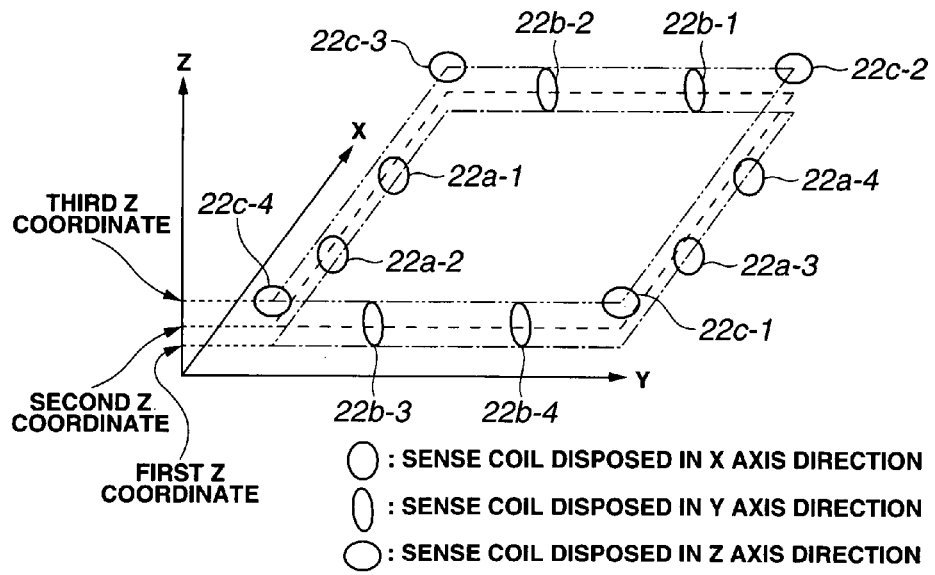
FIG. 2 is a view illustrating an example of arrangement of coils embedded in the coil unit of FIG. 1.
Figure 3:
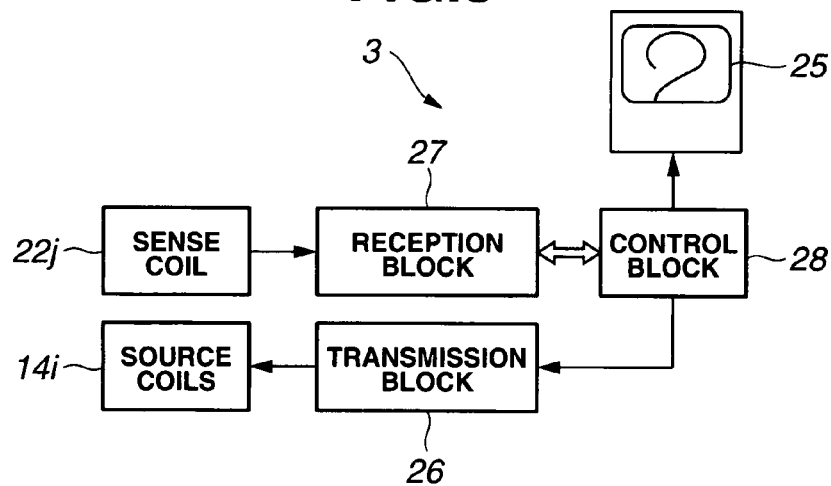
FIG. 3 is a configuration view illustrating a configuration of the endoscope shape detection device of FIG. 1.
Figure 4:
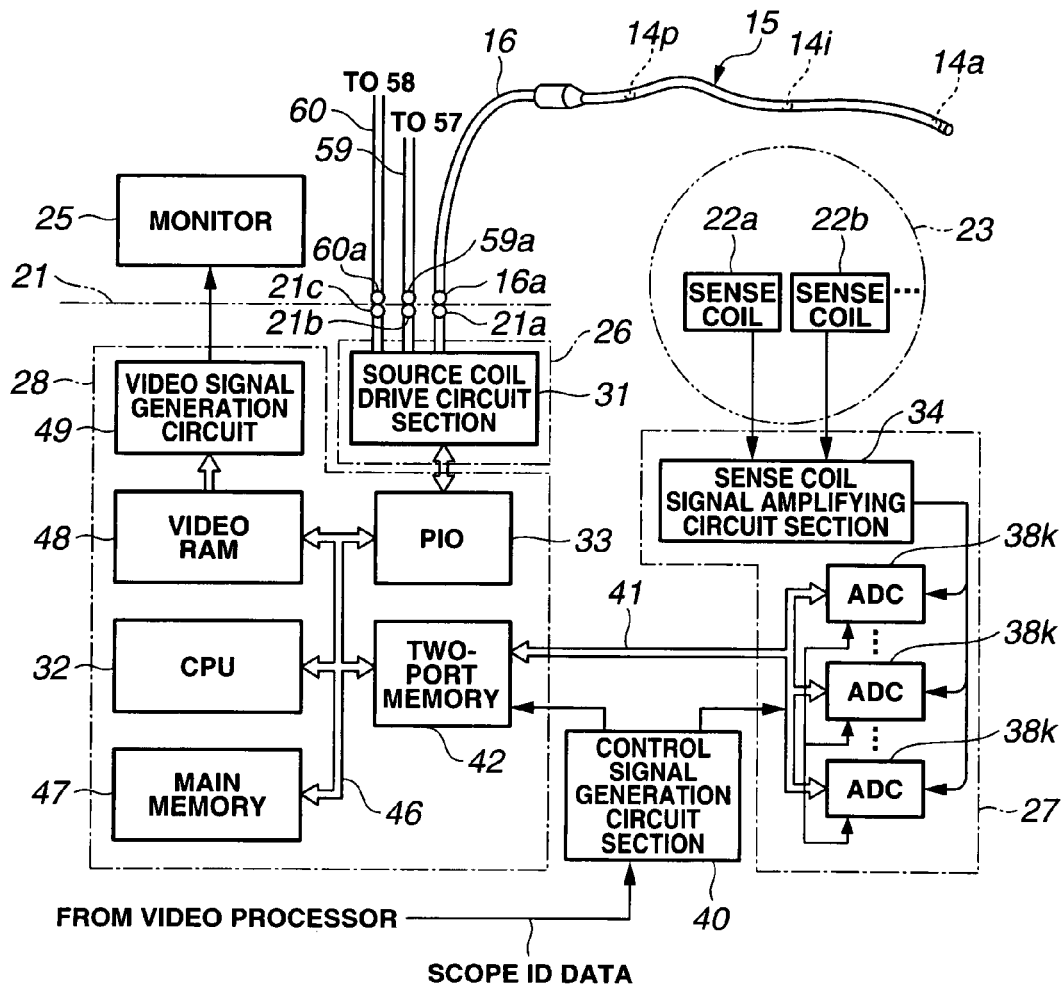
FIG. 4 is a view illustrating configurations of the reception block and the control block of FIG. 3.
Figure 5:
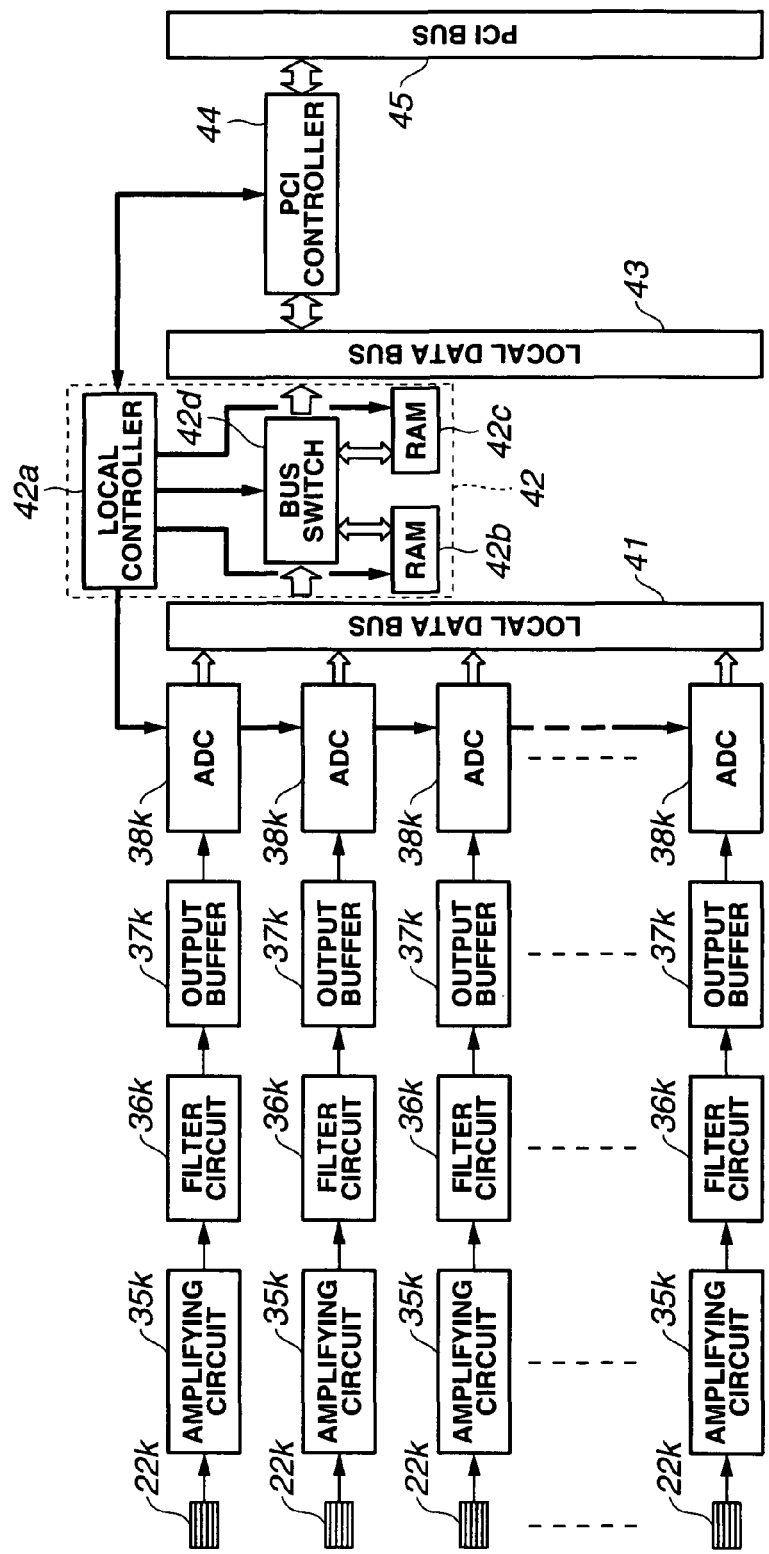
FIG. 5 is a view illustrating a detailed configuration of the reception block of FIG. 3.
Figure 6:
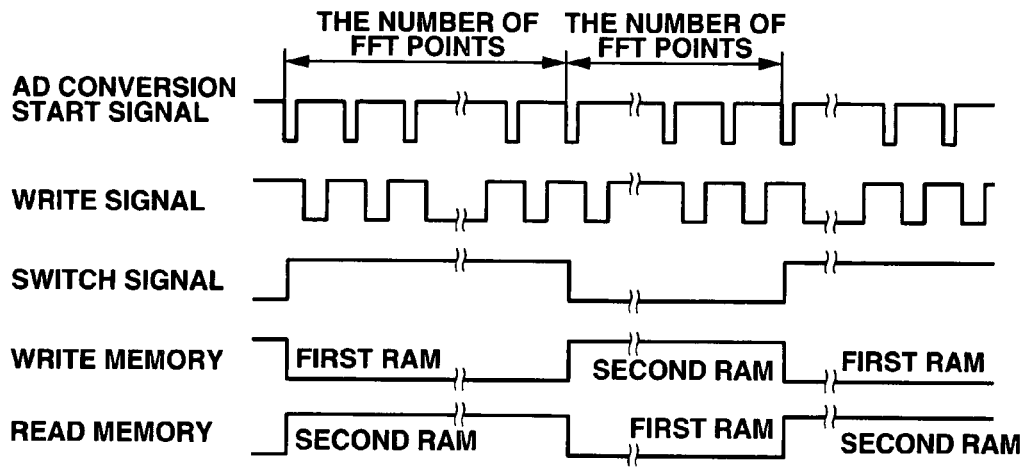
FIG. 6 is a timing chart illustrating an operation of the two-port memory, or the like of FIG. 4.
Figure 7:
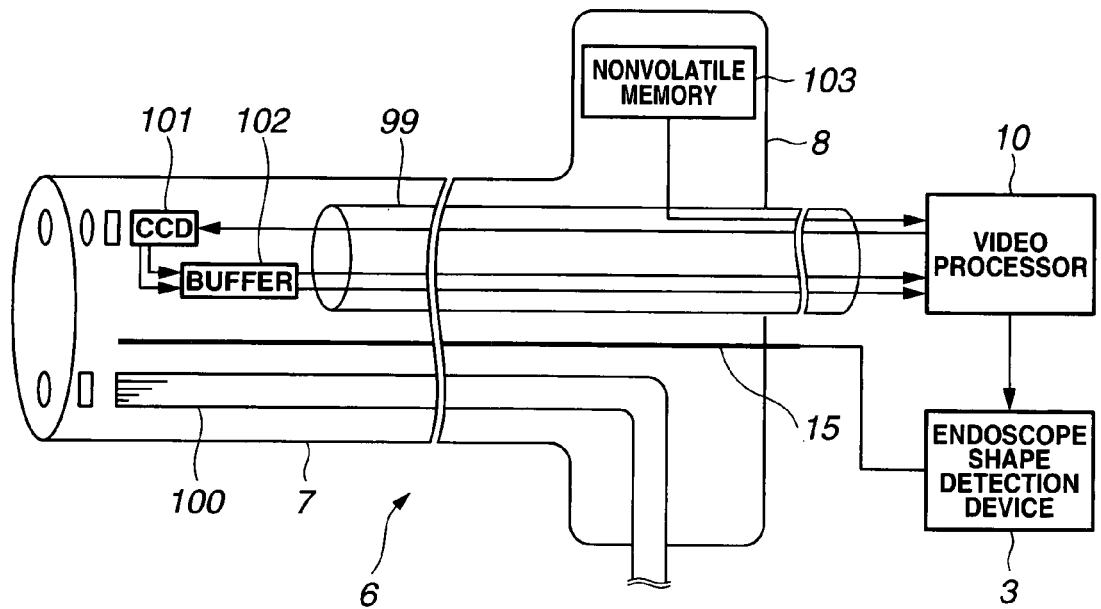
FIG. 7 is a view illustrating a configuration of the electronic endoscope of FIG. 1.
Figure 8:
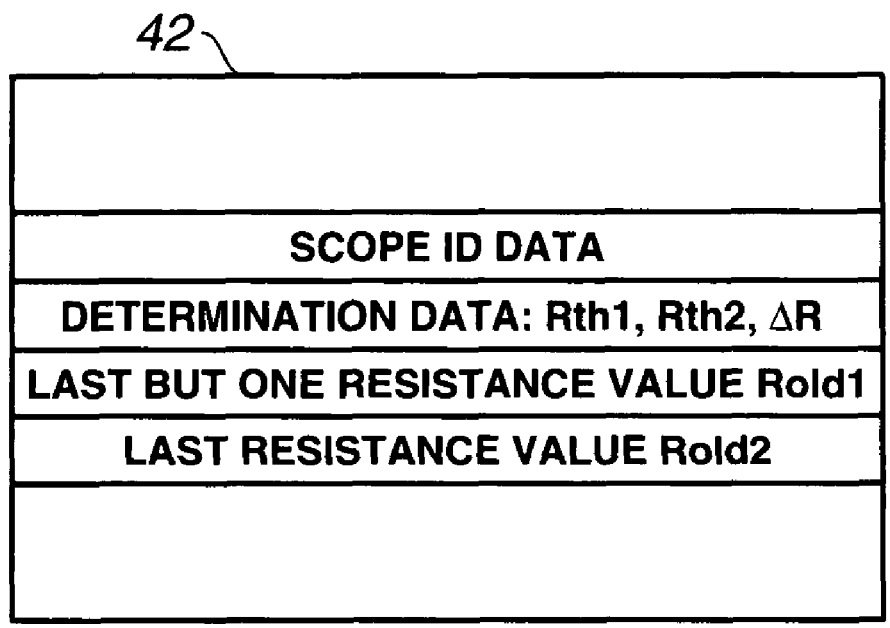
FIG. 8 is a view illustrating a memory map of the two-port memory of FIG. 4.
Figure 9:
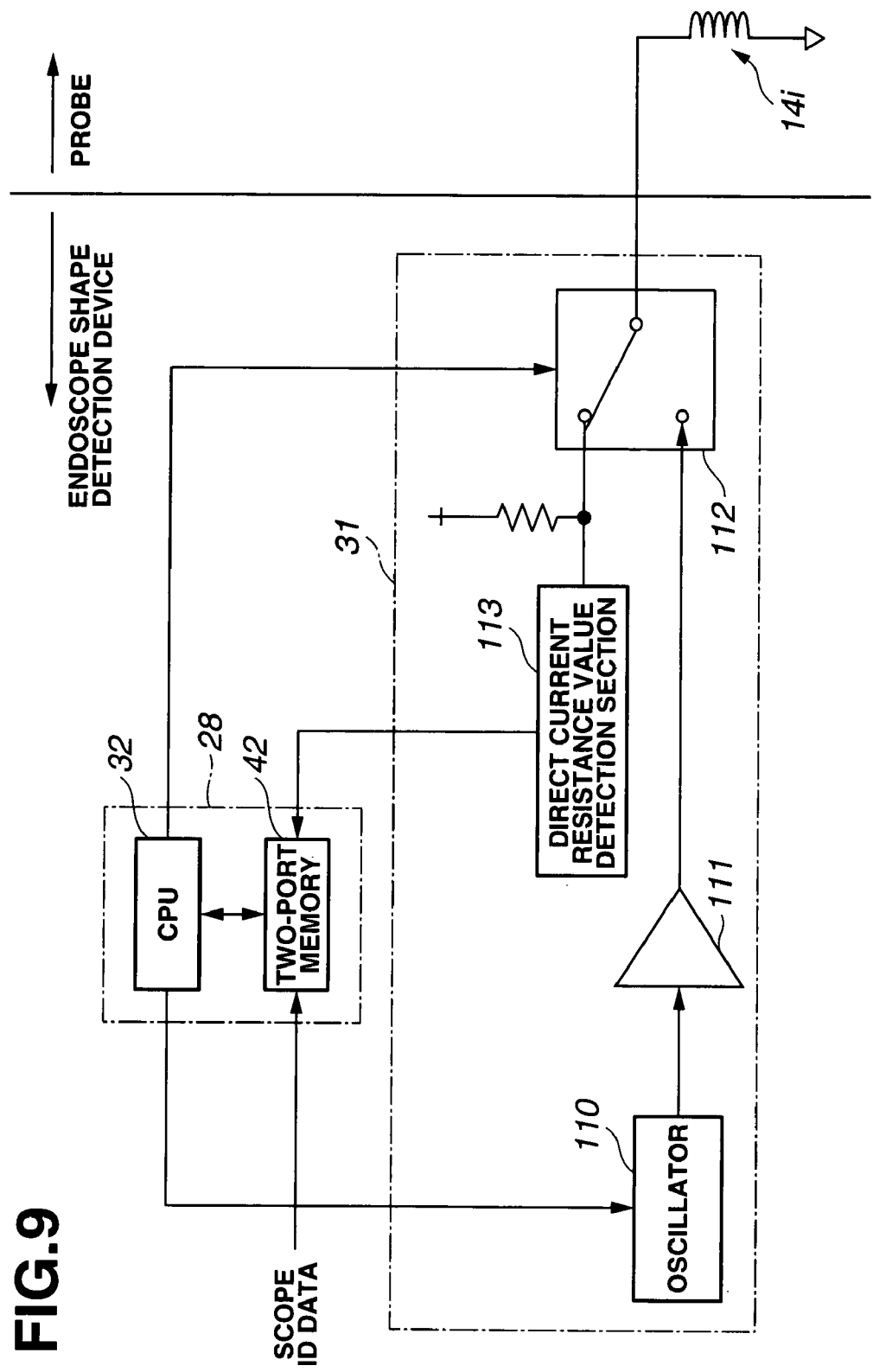
FIG. 9 is a view illustrating a configuration of the source coil drive circuit section of FIG. 4.
Figure 10:
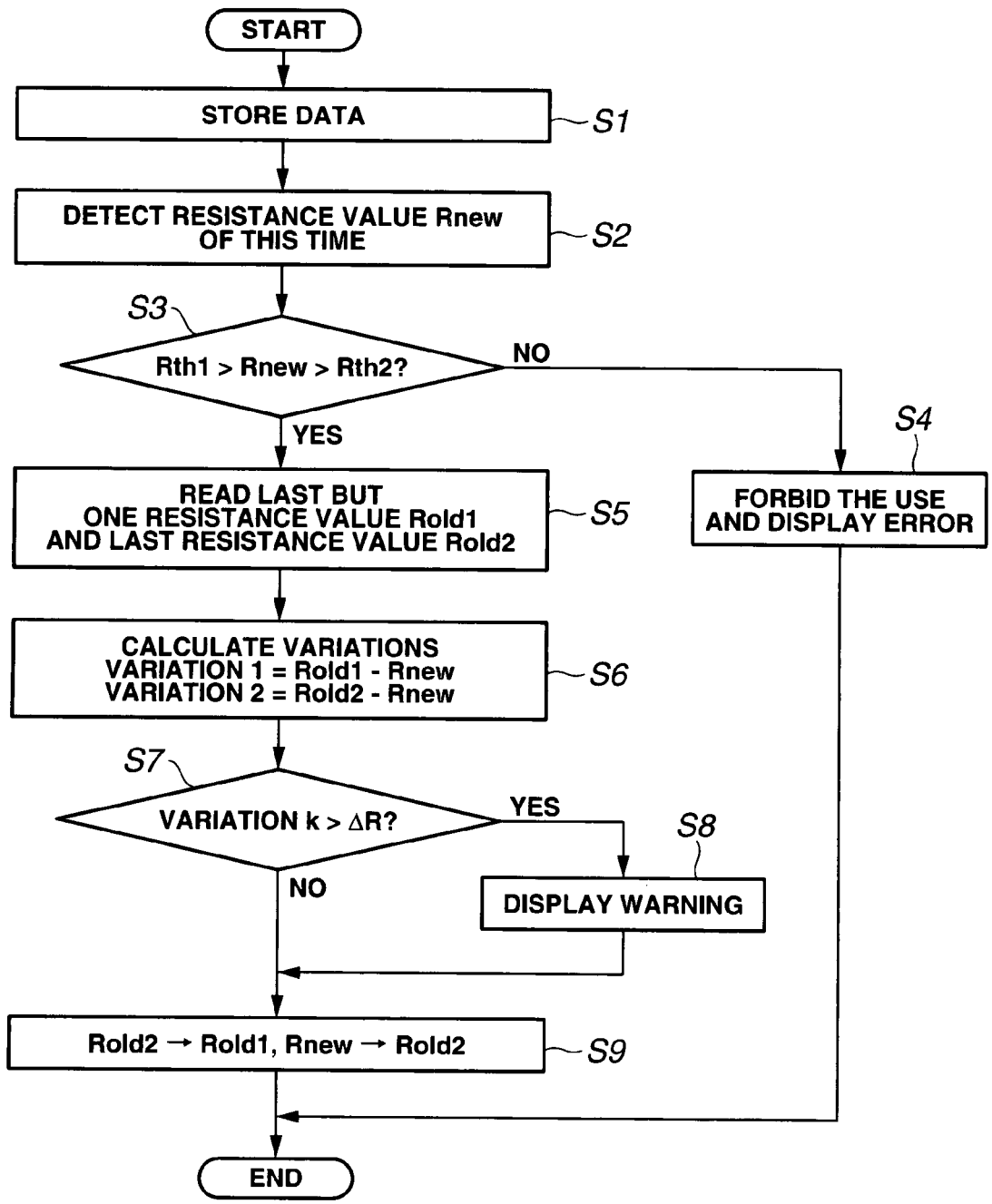
FIG. 10 is a flowchart for explaining an operation of the endoscope system of FIG. 3.
Figure 11:
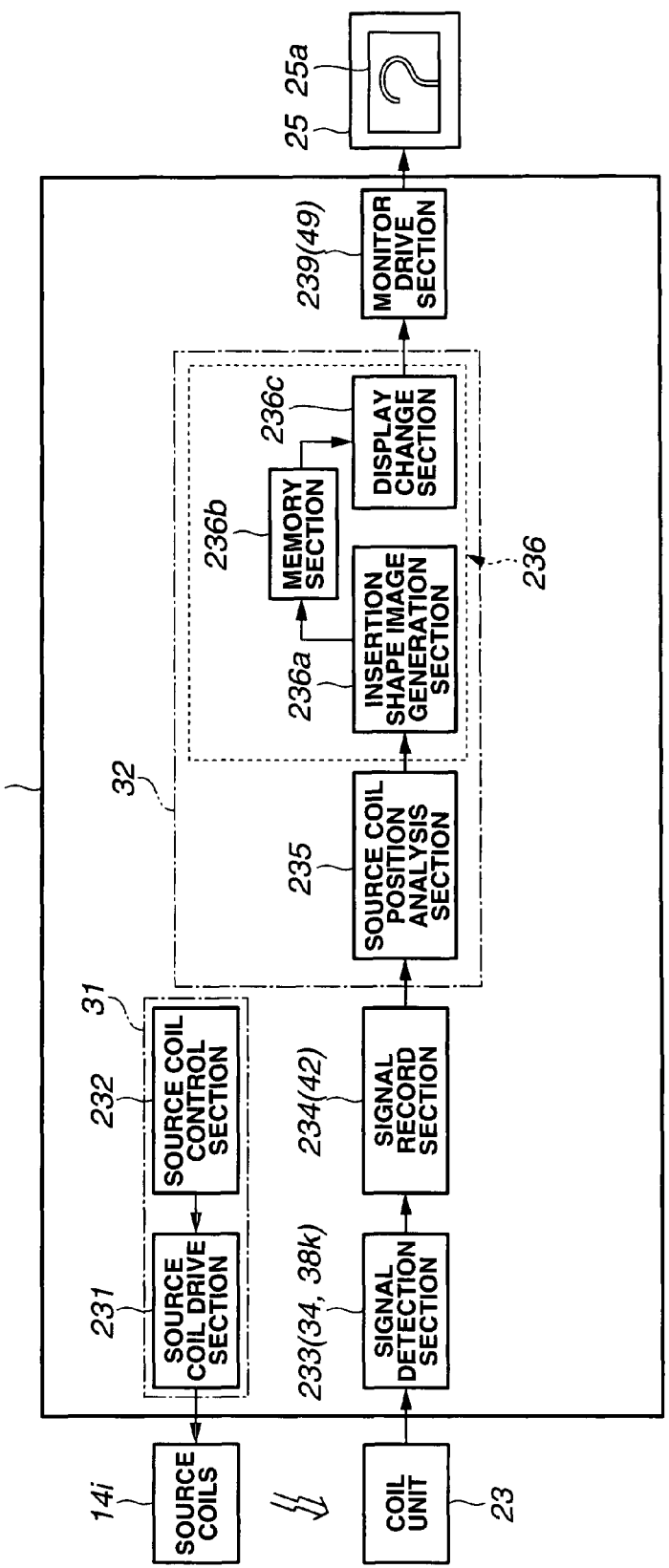
FIG. 11 is a block diagram illustrating an internal functional configuration of the endoscope shape detection device of FIG. 1.
Figure 12:
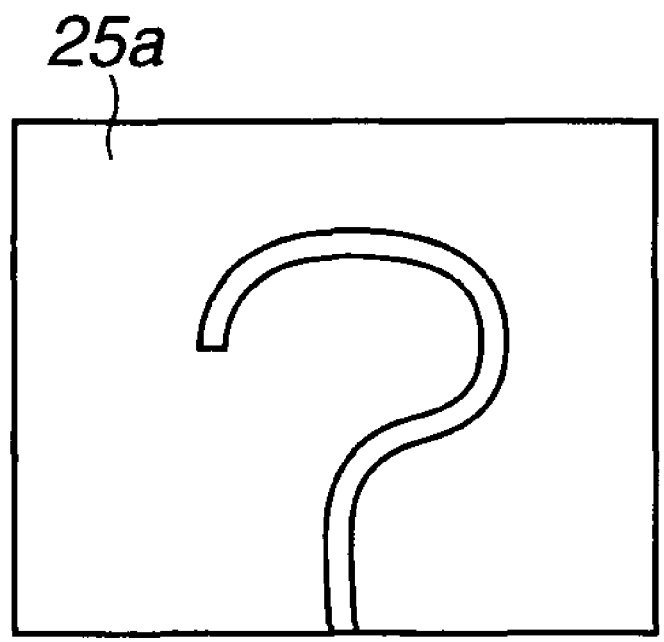
FIG. 12 is a view illustrating an example of a figure of an insertion shape drawn on a monitor screen with the endoscope shape detection device of FIG. 1.
Figure 13:
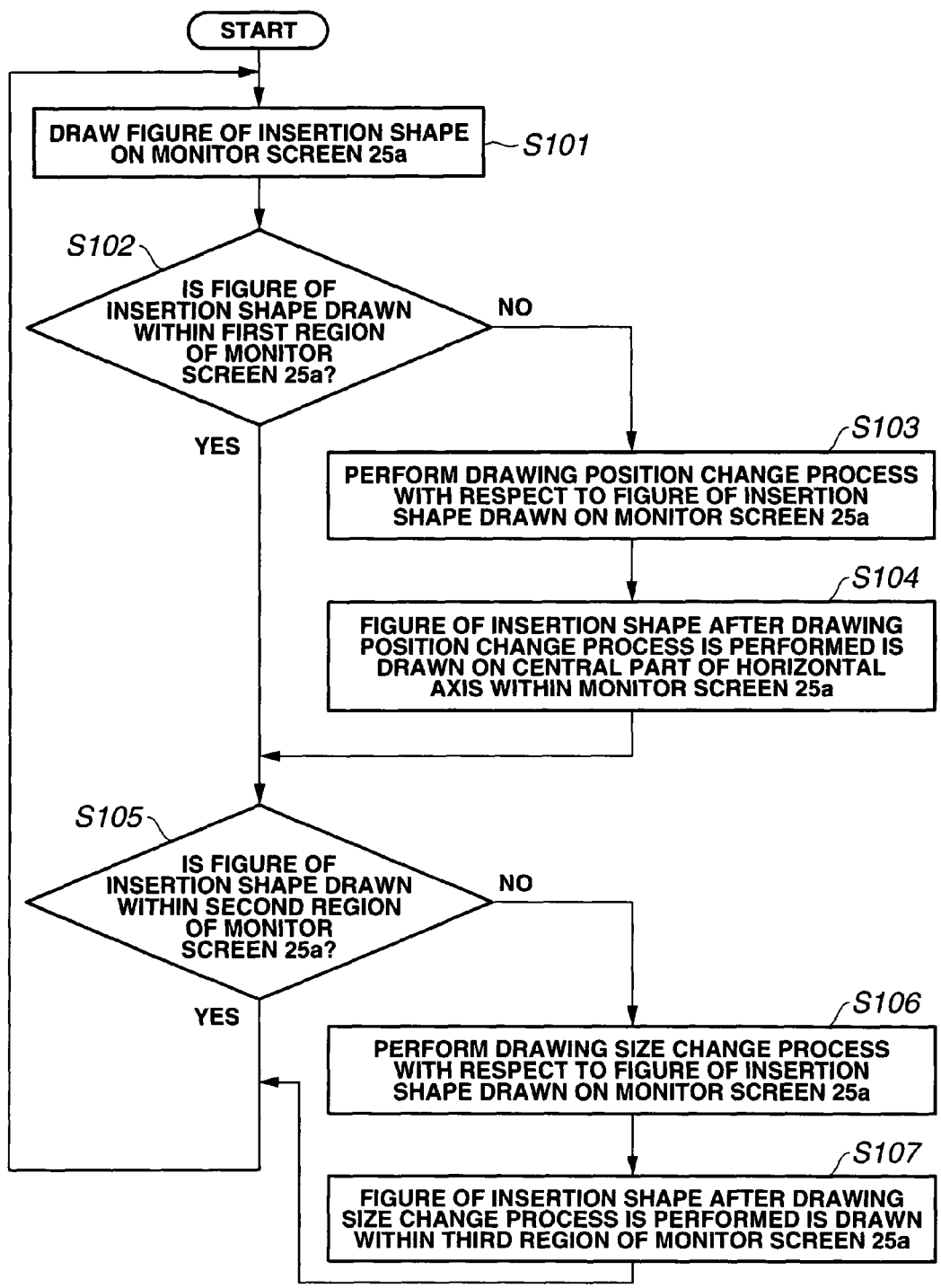
FIG. 13 is a flowchart illustrating a display control performed by the endoscope shape detection device of FIG. 1.
Figure 14:
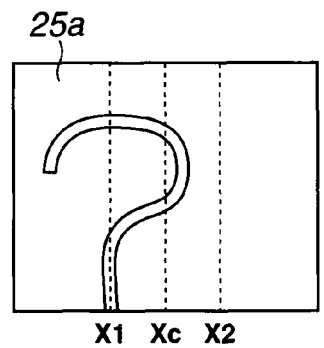
FIG. 14 is a view illustrating a state in which a figure of an insertion shape of an insertion part according to the first embodiment is drawn outside a first predetermined region on the monitor screen.
Figure 15:
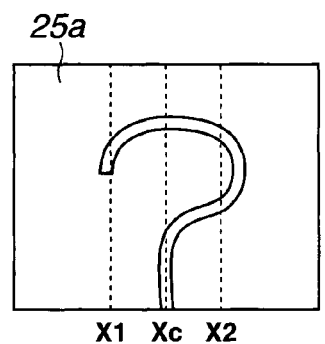
FIG. 15 is a view illustrating a state after a first display change process is performed with respect to the figure of the insertion shape shown in FIG. 14.
Figure 16:
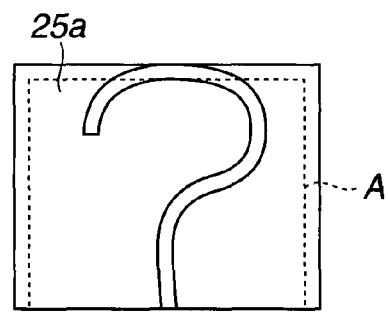
FIG. 16 is a view illustrating a state in which a figure of an insertion shape of the insertion part according to the first embodiment is drawn outside a second predetermined region on the monitor screen.
Figure 17:
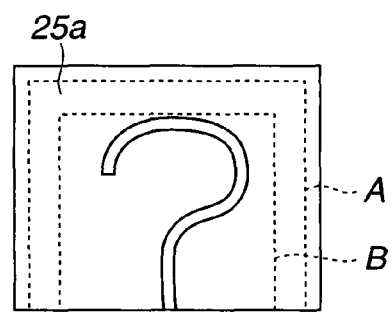
FIG. 17 is a view illustrating a state after a second display change process is performed with respect to the figure of the insertion shape shown in FIG. 16.

FIGS. 1 to 17 relate to the first embodiment of the present invention. FIG. 1 is a configuration view illustrating a configuration of an endoscope system, FIG. 2 is a view illustrating an example of arrangement of coils embedded in the coil unit of FIG. 1, and FIG. 3 is a configuration view illustrating a configuration of the endoscope shape detection device of FIG. 1. FIG. 4 is a view illustrating configurations of the reception block and the control block of FIG. 3, FIG. 5 is a view illustrating a detailed configuration of the reception block of FIG. 3, and FIG. 6 is a timing chart illustrating an operation of the two-port memory, or the like of FIG. 4. FIG. 7 is a view illustrating a configuration of the electronic endoscope of FIG. 1, FIG. 8 is a view illustrating a memory map of the two-port memory of FIG. 4, and FIG. 9 is a view illustrating a configuration of the source coil drive circuit section of FIG. 4. FIG. 10 is a flowchart for explaining an operation of the endoscope system of FIG. 3, FIG. 11 is a block diagram illustrating an internal functional configuration of the endoscope shape detection device of FIG. 1, and FIG. 12 is a view illustrating an example of a figure of an insertion shape drawn on a monitor screen with the endoscope shape detection device of FIG. 1. FIG. 13 is a flowchart illustrating a display control performed by the endoscope shape detection device of FIG. 1, FIG. 14 is a view illustrating a state in which a figure of an insertion shape of an insertion part according to the first embodiment is drawn outside a first predetermined region on the monitor screen, and FIG. 15 is a view illustrating a state after a first display change process is performed with respect to the figure of the insertion shape shown in FIG. 14. FIG. 16 is a view illustrating a state in which a figure of the insertion shape of the insertion part is drawn outside a second predetermined region on the monitor screen, and FIG. 17 is a view illustrating a state after a second display change process is performed with respect to the figure of the insertion shape shown in FIG. 16.

As shown in FIG. 1, an endoscope system 1 according to the present embodiment includes an endoscope device 2 that performs endoscopies and an endoscope shape detection device 3 that is subsidiarily used for endoscopies. The endoscope shape detection device 3 is used as insertion auxiliary means in an endoscopy that is performed by inserting an insertion part 7 of an electronic endoscope 6 into a body cavity of a patient 5 who is lying on a bed 4.

The electronic endoscope 6 has an operation part 8 having a bending operation knob at a rear end of the flexible and elongated insertion part 7. From the operation part 8, a universal cord 9 extends and is connected to a video processor 10.

The electronic endoscope 6 transmits illumination light emitted from a light source part in the video processor 10 through which a light guide is inserted, and, from a illumination window that is provided at a distal end part of the insertion part 7, emits the transmitted light to illuminate the patient, or the like. An image of the illuminated subject, for example, an affected part, is formed on an image pickup element (CCD) disposed on the image forming position with an objective lens mounted on an observation window provided adjacent to the illumination window. The image pickup element photoelectrically converts the formed subject image.

Specifically, in a distal end part 200 that is the distal end part of the insertion part 7, an object optical system 201 that forms an image of a subject and a CCD (charge-coupled device) 101 that captures the image of the subject formed with the object optical system 201 and outputs the captured image of the subject as an image pickup signal are provided. The image pickup signal outputted from the CCD 101 is outputted to a signal line 99 that is connected to a rear of the CCD 101 at one end. The signal line 99 is provided so as to be inserted through the inside of the insertion part 7, the operation part 8, and the universal cord 16, and the other end is electrically connected to the video processor 10. Accordingly, the image pickup signal outputted from the CCD 101 is outputted to the video processor 10 through the signal line 99.

The electric signal of the photoelectrically converted subject image is processed by a video signal processing section in the video processor 10. Then, a standard video signal is generated by the video signal processing section and the signal is displayed on an image observation monitor 11 that is connected to the video processor 10.

The electronic endoscope 6 includes a forceps channel 12. From an insertion opening 12a of the forceps channel 12, for example, a probe 15 that has sixteen magnetic field generation elements (or source coils) 14a, 14b ..., 14p (hereinafter, represented by a reference numeral 14i) is inserted through, and then, the source coils 14i are installed in the insertion part 7.

In a source cable 16 that extends from the rear end of the probe 15, a connector 16a that is a rear end of the source cable 16 is detachably connected to a detection device (also, referred to as a device body) 21 that is a device body of the endoscope shape detection device 3. Then, the source coils 14i generate magnetic fields when a drive signal is applied from the side of the detection device 21 to the source coils 14i that are to be magnetic field generation means through the source cable 16 that is drive signal transmission means.

To the detection device 21 that is disposed in the vicinity of the bed 4 on which the patient 5 is lying, a (sense) coil unit 23 is vertically movably (capable of freely rising and falling)

provided. In the coil unit 23, a plurality of magnetic field detection elements (sense coils) are disposed.

More particularly, as shown in FIG. 2, for example, twelve sense coils (hereinafter, represented by a reference numeral 22$j$), that is, sense coils 22$a$-1, 22$a$-2, 22$a$-3, and 22$a$-4 that have a central z-coordinate of a first z-coordinate and face to the X axis, sense coils 22$b$-1, 22$b$-2, 22$b$-3, and 22$b$-4 that have a central z-coordinate of a second z-coordinate, which is different from the first z-coordinate, and face to the Y axis, and sense coils 22$c$-1, 22$c$-2, 22$c$-3, and 22$c$-4 that have a central z-coordinate of a third z-coordinate, which is different from the first and the second z-coordinates, and face to the Z axis, are disposed.

The sense coils 22$j$ are connected to the detection device 21 through a cable (not shown) that extends from the coil unit 23. The detection device 21 includes an operation panel 24 that is used by a user to operate the device. On an upper part of the detection device 21, a liquid crystal monitor 25 that has a monitor screen 25$a$ is disposed as display means for displaying a shape (hereinafter, referred to as a scope model) of a detected endoscope insertion part.

The endoscope shape detection device 3, as shown in FIG. 3, includes a transmission block 26 that drives the source coils 14$i$, a reception block 26 that receives a signal detected by the sense coils 22$j$ in the coil unit 23, and a control block 28 that processes the signal received by the reception block 27.

As shown in FIG. 4, in the probe 15 that is installed in the insertion part 7 of the electronic endoscope 6, as described above, the sixteen source coils 14$i$ for generating magnetic fields are disposed at the predetermined intervals. These source coils 14$i$ are connected to a source coil drive circuit section 31 that generates sixteen drive signals that have different frequencies respectively and forms the transmission block 26.

The source coil drive circuit section 31 drives each of the source coils 14$i$ with the each drive signal of a sine wave of the different frequency. The each drive frequency is set by drive frequency setting data (also referred to as drive frequency data) stored on drive frequency setting data storage means or drive frequency setting data recording means (not shown) in the source coil drive circuit section 31. The drive frequency data is stored on drive frequency data storage means (not shown) in the source coil drive circuit section 31 through a parallel input/output circuit (PIO) 33 with a CPU (central processing unit) 32 that functions as shape estimation means for performing a process of the endoscope shape calculation or the like in the control block 28.

Meanwhile, the twelve sense coils 22$j$ in the coil unit 23 are connected to a sense coil signal amplifying circuit section 34 that forms the reception block 27.

In the sense coil signal amplifying circuit section 34, as shown in FIG. 5, each of twelve single-core coils 22$k$ that form the sense coils 22$j$ is connected to each amplification circuit 35$k$, and, thus, twelve processing systems are formed. Feeble signals detected by the each of the single-core coils 22$k$ are amplified by the amplification circuits 35$k$, unwanted components are cleared in filter circuits 36$k$ with a bandwidth through which a plurality of frequencies generated by the source coil group pass, and the signals are outputted to output buffers 37$k$. Then, the signals are converted into digital signals that are readable in the control block 28 by analog-digital converters (ADC) 38$k$.

The reception block 27 includes the sense coil signal amplifying circuit section 34 and the ADCs 38$k$. The sense coil signal amplifying circuit section 34 includes the amplification circuits 35$k$, the filter circuits 36$k$, and the output buffers 37$k$.

Turning now to FIG. 4, the outputs of the twelve systems of the sense coil signal amplifying circuit section 34 are transmitted to the twelve ADCs 38$k$, and converted into digital data of a predetermined sampling period by a clock supplied from a control signal generation circuit section 40 that functions as numeric value data write means in the control block 28. The digital data is written on a two-port memory 42 that functions as data output means through a local data bus 41 by a control signal supplied from the control signal generation circuit section 40.

The two-port memory 42, as shown in FIG. 5, functionally includes a local controller 42$a$, a first RAM 42$b$, a second RAM 42$c$, and a bus switch 42$d$. With timing shown in FIG. 6, in response to an A/D conversion start signal from the local controller 42$a$, the ADCs 38$k$ start A/D conversions, the bus switch 42$d$ switches the RAM 42$b$ and the RAM 42$c$ by switch signals from the local controller 42$a$ to alternately use the RAMs 42$b$ and 42$c$ as a read memory or a write memory, and by a write signal, after the power is supplied, the data is continuously taken in the memory.

Turning again to FIG. 4, the CPU 32 reads the digital data written on the two-port memory 42 with the control signal supplied from the control signal generation circuit section 40 through an internal bus 46 that has a local data bus 43, a PCI controller 44, and a PCI bus 45 (see FIG. 5). Then, the CPU 32 uses a main memory 47 to perform a frequency extraction process (fast Fourier transform: FFT) with respect to the digital data, and separates and extracts the data as magnetic field detection information of frequency components corresponding to the drive frequencies of the each of the source coils 14$i$. Based on the each digital data of the separated magnetic field detection information, spatial positional coordinates of the each of the source coils 14$i$ disposed in the probe 15 inserted into the insertion part 7 of the electronic endoscope 6 are calculated.

Based on the calculated spatial positional coordinate data, an insertion state of the insertion part 7 of the electronic endoscope 6 is estimated, display data for forming a scope model is generated, and the data is outputted to a video RAM 48. The data written on the video RAM 48 is read by a video signal generation circuit 49, the data is converted into an analog video signal, and then, outputted to the liquid crystal monitor 25. The liquid crystal monitor 25, in response to the input of the analog video signal, displays a scope model of the insertion part 7 of the electronic endoscope 6 on the display screen.

In the CPU 32, the magnetic field detection information corresponding to the each of the source coils 14$i$, that is, electromotive force (amplitude values of sinusoidal signals) generated in the single-core coils 22$k$ that form the each of the sense coils 22$j$ and phase information is calculated. The phase information shows polar characters ± of the electromotive force.

In the embodiment, as shown in FIG. 1, in order to check a position of the insertion part 7 being inserted into the body, an extracorporeal marker 57 for displaying the position outside the body and a reference plate 58 to be used by attaching on an abdominal part or the like of the patient 5 to always display a scope model from a certain direction (of the patient 5) even if a body position of the patient 5 changes may be connected to the detection device 21 and used.

The extracorporeal marker 57 includes a source coil inside the marker and a connector 59$a$ of a base end of a cable 59 of the extracorporeal marker 57 is detachably connected to the detection device 21.

In response to the connection of the connector 59$a$, the source coil of the extracorporeal marker 57 is driven similarly to the case of the source coils in the probe 15, and the position of the source coil of the extracorporeal marker 57 is displayed on the monitor 25 similarly to the scope model.

The reference plate 58 includes, for example, three source coils inside a disk-shaped part of the plate, and a connector 60a of a base end of a cable 60 connected to these three source coils is detachably connected to the detection device 21.

Based on positional detection of these three coils, a surface on which these coils are disposed is determined. Then, the reference plate 58 is used to draw a scope model for an observation so that the insertion part 7 is viewed from a direction perpendicular to the surface.

Further, as shown in FIG. 4, in the present embodiment, to the detection device 21, connector receptors 21a, 21b, and 21c to which the connector 16a of the probe 15, the connector 59a of extracorporeal marker 57, and the connector 60a of the reference plate 58 are connected respectively are provided. Each of the connector receptors 21a, 21b, and 21c is connected to the source coil drive circuit 31.

As shown in FIG. 7, in the electronic endoscope 6, a light guide 100 that transmits illumination light to the insertion part 7 and the probe 15 that has the plurality of source coils 14i are disposed. Further, in the distal end part of the insertion part 7, the CCD 101 that captures an image of a subject is provided. Then, in response to a drive signal from the video processor 10, the CCD 101 is driven and the image pickup signal captured by the CCD 101 is transmitted to the video processor 10 through a buffer circuit 102. The drive signal and the image pickup signal are transmitted and/or received between the video processor 10 and the CCD 101 with the signal line 99 that is inserted into the insertion part 7.

Meanwhile, in the operation part 8 of the base end side of the electronic endoscope 6, a nonvolatile memory 103 is provided. On the nonvolatile memory 103, scope ID data for identifying the electronic endoscope 6 and various determination data for determining a state of the source coils 14i that are provided in the probe 15 is stored. The nonvolatile memory 103 includes an electrically rewritable flash memory (R) or the like.

The scope ID data and the various determination data is taken in the endoscope shape detection device 3 through the video processor 10 on startup of the endoscope system 1. The endoscope shape detection device 3, as shown in FIG. 8, through the control signal generation circuit section 40, stores the scope ID data and the various determination data (Rth1, Rth2, $\Delta R$), for example, on a predetermined address region of the two-port memory 42 (see FIG. 4).

The source coil drive circuit section 31 of the endoscope shape detection device 3 includes, as shown in FIG. 9, an oscillator 110 that generates a sine wave and an amplifier 111 that amplifies the sine wave and generates (drives) an alternating magnetic field to the source coils 14i through a switch section 112. The switch section 112 is configured to switch a direct current to an output of the amplifier 111 and supply to the source coils 14i. In the source coil drive circuit section 31, a direct current resistance value detection section 113 for measuring a direct current resistance value of the source coils 14i by voltage drop when the switch section 112 is supplying the direct current to the source coils 14i is provided.

The source coil drive circuit section 31 includes a plurality of the oscillators 110, the amplifiers 111, the switch sections 112, and the direct current resistance value detection sections 113 corresponding to the source coils 14, and while drives the plurality of source coils 14i, measures the direct current resistance values of the plurality of source coils 14. A plurality of times of measured direct current resistance values, for example, two times of direct current resistance values Rold1, Rold2 are stored on the predetermined address region of the two-port memory 42 (see FIG. 8).

Now, thus configured endoscope shape detection process according to the present embodiment will be described.

When the endoscope system 1 is started up, the video processor 10 reads the scope ID data and the various determination data (Rth1, Rth2, $\Delta R$) from the nonvolatile memory 103 of the electronic endoscope 6, and transmits the scope ID data and the various determination data (Rth1, Rth2, $\Delta R$) to the endoscope shape detection device 3.

As shown in FIG. 10, at step S1, the CPU 32 of the endoscope shape detection device 3 stores the scope ID data and the various determination data (Rth1, Rth2, $\Delta R$) on the predetermined address region of the two-port memory 42 through the control signal generation circuit section 40 (see FIG. 8).

Then, at step S2, the CPU 32 of the endoscope shape detection device 3 controls the switch section 112 to supply a direct current to the source coils 14i, and detects a direct current resistance value Rnew of the source coils 14i by the direct current resistance value detection section 113. The CPU 32 determines whether the resistance value Rnew detected at step S3 satisfies Rth1<Rnew<Rth2 with respect to the determination data Rth1 and Rth2. In a case that it is determined that Rth1<Rnew<Rth2 is not satisfied, the CPU 32 determines that the source coils 14i are broken or short-circuited, and then, at step S4, forbids the use of the probe 15, displays an error on the monitor 25, and finishes the process.

In a case that it is determined that Rth1<Rnew<Rth2 is satisfied, at step S5, the CPU 32 reads past values as reference values, for example, a last but one detected direct current resistance value Rold1 and a last detected direct current resistance value Rold2 from the two-port memory 42. Then, at step S6, the CPU 32 calculates differences between the resistance value Rold1 and the resistance value Rold2 and the resistance value Rnew, that is, a variation 1=|Rold1−Rnew|, and a variation 2=|Rold2−Rnew|.

At step S7, the CPU 32 compares the variation 1 or the variation 2 to the determination data $\Delta R$ to determine whether either variation 1>$\Delta R$ or variation 2>$\Delta R$ is satisfied. The variation 1 and the variation 2 indicate variation of resistance values of the source coils 14i over time.

In a case that the CPU 32 determines either variation 1>$\Delta R$ or variation 2>$\Delta R$ is satisfied, it is considered that the source coils 14i are likely to break or short-circuit. Then, at step S8, the CPU 32 displays a warning for urging to replace the probe 15, or the like, on the monitor 25, and the process proceeds to step S9. In a case that both the variation 1 and variation 2 are within the $\Delta R$, the process directly proceeds from step S7 to step S9.

At step S9, the CPU 32 rewrites the last but one resistance value to the Rold2, and the last resistance value to the Rnew in the two-port memory 42, and finishes the process.

The above processes are time-sharingly performed with respect to all sixteen source coils 14i. Since the sixteen source coils 14i are time-sharingly magnetic-field driven at the time of shape detection, within the above processes, in the period that the sixteen source coils 14i are not magnetic-field driven, processes of steps S2 to S9 may be time-sharingly and continuously performed with respect to the all sixteen source coils 14i. Further, when the shape detection process is finished, the resistance values Rold1 and Rold2 being stored finally on the two-port memory 42 may be stored on the nonvolatile memory 103 of the electronic endoscope 6 and the nonvolatile memory 103 may be rewritten.

As described above, in the present embodiment, the direct current resistance values (electronic property) of the each source coil are detected and the state of the source coils can be determined. Accordingly, variation of the probe over time can be monitored based on the determined result, and the probe can be appropriately managed.

Incidentally, in endoscope shape detection devices proposed in, for example, Japanese Patent No. 3290153, it is assumed that a part of a figure of an insertion shape of an insertion part to be displayed on a monitor that functions as a display section may be outside a display region of the monitor, and the whole figure may not be displayed. In such a case, the operator, with respect to the insertion part outside the display and not displayed part in the figure of the insertion shape of the insertion part, cannot see the state thereof.

In the embodiment, in the case that a part of a figure of an insertion shape to be drawn by an endoscope shape detection device is drawn on a region outside a predetermined region of a display part, by performing a display change process, the figure of the insertion shape can be drawn in the region of the display part. Hereinafter, a detailed description will be made with reference to FIGS. 1, and 11 to 17.

As shown in FIG. 1, the operation panel 24 being provided on an outer surface of the endoscope shape detection device 3 includes a plurality of switches, for example, an automatic/manual changing-over switch configured to switch a timing that the endoscope shape detection device 3 performs a first display change process and a second display change process either automatically or manually, a switch configured to instruct a timing to manually perform the first and second display change processes with respect to the endoscope shape detection device 3, or the like. In a case that the operator manually performs the first and second display change processes, after the operator sets the automatic/manual change-over switch to manual, by depressing the switch at a desired timing, the first and second display change processes are performed. With respect to the first and second display change processes, a detailed description will be made below. In descriptions of the present embodiment below, with respect to the first and second display change processes, a timing the endoscope shape detection device 3 performs the first and second display change processes is set to automatic.

As shown in FIG. 11, the endoscope shape detection device 3 includes the above-described source coil drive circuit section 31 that has a source coil drive section 231 for driving the source coils 14i and a source coil control section 232 for controlling a magnetic field generation timing, frequencies, or the like, of the source coils 14i through the source coil drive section 231, a signal detection section 233 that has the above-described sense coil signal amplifying circuit section 34 and the ADCs 38k, a signal recording section 234 that has the above-described two-port memory 42, a source coil position analysis section 235 and an image generation section 236 that are realized by the above-described CPU 32, and a monitor drive section 239 that has the above-described video signal generation circuit 49. The image generation section 236 includes an insertion shape image generation section 236a, a memory section 236b, and a display change section 236c.

The signal detection section 233 that functions as a detection section detects a magnetic field signal outputted from the coil unit 23, amplifies the magnetic field signal to a signal processable level, and outputs the signal.

The signal recording section 234 temporarily records the magnetic field signal outputted from the signal detection section 233.

The source coil position analysis section 235 analyzes three-dimensional positional coordinates of the source coils 14i based on the magnetic field signal recorded on the signal recording section 234, and outputs the analyzed information as a three-dimensional positional coordinate information signal.

The insertion shape image generation section 236a calculates a three-dimensional shape of the insertion part 7 based on the three-dimensional positional coordinate information signal of the source coils 14i outputted from the source coil position analysis section 235. Further, the insertion shape image generation section 236a generates a figure of the insertion shape of the insertion part 7 based on the calculated three-dimensional shape of the insertion part 7, and outputs the information as an insertion shape figure signal that is an image signal.

Then memory section 236b temporarily records the insertion shape figure signal of the insertion part 7 outputted from the insertion shape image generation section 236a.

The display change section 236c, based on the insertion shape figure signal recorded on the memory section 236b, so that a part or the whole of the insertion shape figure of the insertion part 7 generated by the insertion shape image generation section 236a is drawn on two-dimensional coordinates within the monitor screen 25a, based on the insertion shape figure signal recorded on the memory section 236b, performs a coordinate correction, and outputs an insertion shape figure signal after the coordinate correction is performed. Further, the display change section 236c, in a case that a part of the insertion shape figure of the insertion part being displayed on the monitor that functions as the monitor section is drawn outside the predetermined region on the monitor screen 25a, performs a predetermined display change process so that the insertion shape figure generated by the insertion shape image generation section 236a based on the insertion shape figure signal recorded on the memory section 236b is to be drawn within the predetermined region in the monitor screen 25a, and outputs an insertion shape figure signal after the predetermined display change process is performed. Detailed descriptions about the first and second display change processes, that is, the predetermined display change process, will be made below.

The monitor drive section 239, based on the insertion shape figure signal outputted from the display change section 236c, drives the monitor 25 to draw the insertion shape figure of the insertion part 7 on the monitor screen 25a.

First, the operator inserts the insertion shape detection probe 15 from the probe insertion opening 12a into the electronic endoscope 6. Then, the operator connects the universal code 9 of the electronic endoscope 6 to the video processor 10, connects the cable 16 of the insertion shape detection probe 15 to the endoscope shape detection device 3, and inserts the insertion part 7 of the electronic endoscope 6 into the body cavity of the patient 5. Then, the CCD 101 captures an image of the inside of the body cavity and outputs the captured image of the inside of the body cavity as an image pickup signal. The video processor 10 performs an image processing or the like based on the image pickup signal outputted from the CCD 101, and outputs an image pickup signal after the image processing or the like is performed to the monitor 11. The monitor 11, based on the image pickup signal outputted from the video processor 10, displays the image of the inside of the body cavity captured by the electronic endoscope 6.

The source coil control section 232 of the endoscope shape detection device 3 controls each of the source coils 14i through the source coil drive section 231 so that the each of the source coils 14i generates a magnetic field at a different timing respectively. The source coils 14i, based on the control content of the source coil control section 232, generates magnetic fields corresponding to the insertion shape of the insertion part 7 in the body cavity. The magnetic fields generated by the source coils 14i are detected by the coil unit 23, and the coil unit 23 outputs a magnetic field signal based on the magnetic fields.

The magnetic field signal outputted from the coil unit 23 is detected in the signal detection section 233 of the endoscope shape detection device 3, amplified to a signal processable level, and outputted. The outputted signal is temporarily recorded on the recording section 234. The source coil position analysis section 235 analyzes three-dimensional positional coordinates of the each of the source coils 14i based on the magnetic field signal recorded on the signal recording section 234, and outputs the analyzed information as three-dimensional positional coordinate information signal. The insertion shape image generation section 236a calculates a three-dimensional shape of the insertion part 7 based on the three-dimensional positional coordinate information signals of the each of source coils 14i outputted from the source coil position analysis section 235, generates a figure of the insertion shape of the insertion part 7 based on the calculated three-dimensional shape of the insertion part 7, and outputs the information as an insertion shape figure signal. Then memory section 236b temporarily records the insertion shape figure signal of the insertion part 7 outputted from the insertion shape image generation section 236a. The display change section 236c, based on the insertion shape figure signal recorded on the memory section 236b, so that a part or the whole of the insertion shape figure of the insertion part 7 generated by the insertion shape image generation section 236a is drawn on two-dimensional coordinates within the monitor screen 25a, performs a coordinate correction, and outputs an insertion shape figure signal after the coordinate correction is performed. The monitor drive section 239, based on the insertion shape figure signal outputted from the display change section 236c, drives the monitor 25, and draws an insertion shape figure of the insertion part 7, for example, as shown in FIG. 12, on the monitor screen 25a (step S101 of FIG. 13: the generation step of the insertion shape figure).

Here, for example, when the operator inserts the insertion part 7 in a deep part of the body cavity, the insertion shape of the insertion part 7 may be drawn as an insertion shape figure shown in FIG. 14. In such a case, the display change section 236c determines whether a central part of a base end side of the insertion shape figure drawn on the monitor screen 25a is drawn, as shown in FIG. 14, within a first region which is between a coordinate X1 and a coordinate X2 including a central part Xc of a horizontal axis in the monitor screen 25a (step S102 of FIG. 13: the position detection step of insertion shape figure). The determination is performed in such a way that, for example, based on a difference between pixel values of the image, a position of a base end side of the insertion shape figure in the horizontal axis direction of the monitor screen 25a is detected, and whether the detected position locates between the coordinate X1 and the coordinate X2 in the horizontal axis direction is determined. The dotted lines drawn in FIGS. 14 and 15 are virtual lines for indicating the first region. Accordingly, the lines are not actually displayed on the monitor screen 25a.

Based on the determination result, in a case that it is determined that the central part of the base end side of the insertion shape figure drawn on the monitor screen 25a is drawn outside the first region, the display change section 236c performs a drawing position change process that corresponds to the first display change process (step S103 of FIG. 13: the step of changing the position of the insertion shape figure), for changing the drawing position of the insertion shape figure based on the insertion shape figure signal recorded on the memory 236b so that the central part of the base end side of the insertion shape figure is drawn in the central part Xc of the horizontal axis within the monitor screen 25a, Then, the display change section 236c outputs an insertion shape figure signal after the drawing position change process is performed. When the monitor drive section 239 drives the monitor 25 based on the insertion shape figure signal outputted from the display change section 236c, on the monitor screen 25a, for example, as shown in FIG. 15, an insertion shape figure of the insertion part 7 after the change of the drawing position is performed is drawn (step S104 of FIG. 13: the step of generating the position change insertion shape figure). In a case that, as shown in FIG. 14, the central part of the base end side of the insertion shape figure drawn on the monitor screen 25a is drawn within the region between the X1 and X2, the above-described drawing position change process is not performed. The coordinates X1 and X2 on the monitor screen 25a are values recorded on a memory (not shown) or the like provided in the display change section 236c. For example, the coordinates X1 and X2 may be values changeable to desired values by the operator by operating the operation panel 24 of the endoscope shape detection device 3 or may be preliminary set fixed values.

Further, for example, in a case that the operator inserts the insertion part 7 in a deep part of the body cavity, the insertion shape of the insertion part 7 may be drawn as an insertion shape figure shown in FIG. 16. In such a case, the display change section 236c determines whether a whole of the insertion shape figure drawn on the monitor screen 25a is drawn within a second region which is a region in a frame A within the monitor screen 25a as shown in FIG. 16 (step S105 of FIG. 13: the size detection step of insertion shape figure). The determination is performed, for example, based on a difference between pixel values of the image, by detecting whether the insertion shape figure is outside the frame A of the monitor screen 25a. The frame A drawn by the dotted line in FIG. 16 is a virtual line for indicating the second region. Accordingly, the line is not actually displayed on the monitor screen 25a.

Based on the determination result, in a case that it is determined that at least a part of the insertion shape figure drawn on the monitor screen 25a is drawn outside the second region, the display change section 236c performs a drawing size change process that corresponds to the second display change process (step S106 of FIG. 13: the step of changing the size of the insertion shape figure) for changing a scale of enlargement of the whole insertion shape figure based on the insertion shape figure signal recorded on the memory section 236b so that the whole of the insertion shape figure is to be drawn within a third region which is a region in a frame B in the monitor screen 25a. Then, the display change section 236c outputs an insertion shape figure signal after the drawing size change process is performed. The frame B drawn by the dotted line in FIG. 17 is a virtual line for indicating the third region. Accordingly, the line is not actually displayed on the monitor screen 25a.

When the monitor drive section 239 drives the monitor 25 based on the insertion shape figure signal outputted from the display change section 236c, on the monitor screen 25a, for example, as shown in FIG. 17, an insertion shape figure of the insertion part 7 after the drawing size is changed is drawn (step S107 of FIG. 13: the step of generating the size change insertion shape figure). In a case that, as shown in FIG. 16, the whole of the insertion shape figure drawn on the monitor screen 25a is drawn within the region in the frame A, the above-described drawing size change process is not performed. The frames A and B on the monitor screen 25a are regions recorded on a memory (not shown) or the like provided in the display change section 236c. For example, the frames A and B may be regions changeable to desired spread, desired positions, or the like by the operator by operating the operation panel 24 of the endoscope shape detection device 3 or may be preliminary set fixed regions.

As described above, in the endoscope shape detection device 3 according to the present embodiment, in the case that the central part of the base end side of the insertion shape figure of the insertion part 7 is drawn outside the first region on the monitor screen 25a, the drawing position change process is performed with respect to the insertion shape figure. Accordingly, the whole of the insertion shape figure can be drawn within the first region. Further, in the endoscope shape detection device 3 according to the present embodiment, as described above, in the case that at least a part of the insertion shape figure of the insertion part 7 is drawn outside the second region of the monitor screen 25a, the drawing size change process is performed with respect to the insertion shape figure. Accordingly, the whole of the insertion shape figure can be drawn within the third region that is narrower than the second region. With the advantages reside in the endoscope shape detection device 3 according to the present embodiment, the operator can perform the insertion operation of the electronic endoscope 6 more smoothly than before.

Second Embodiment

Figure 18:
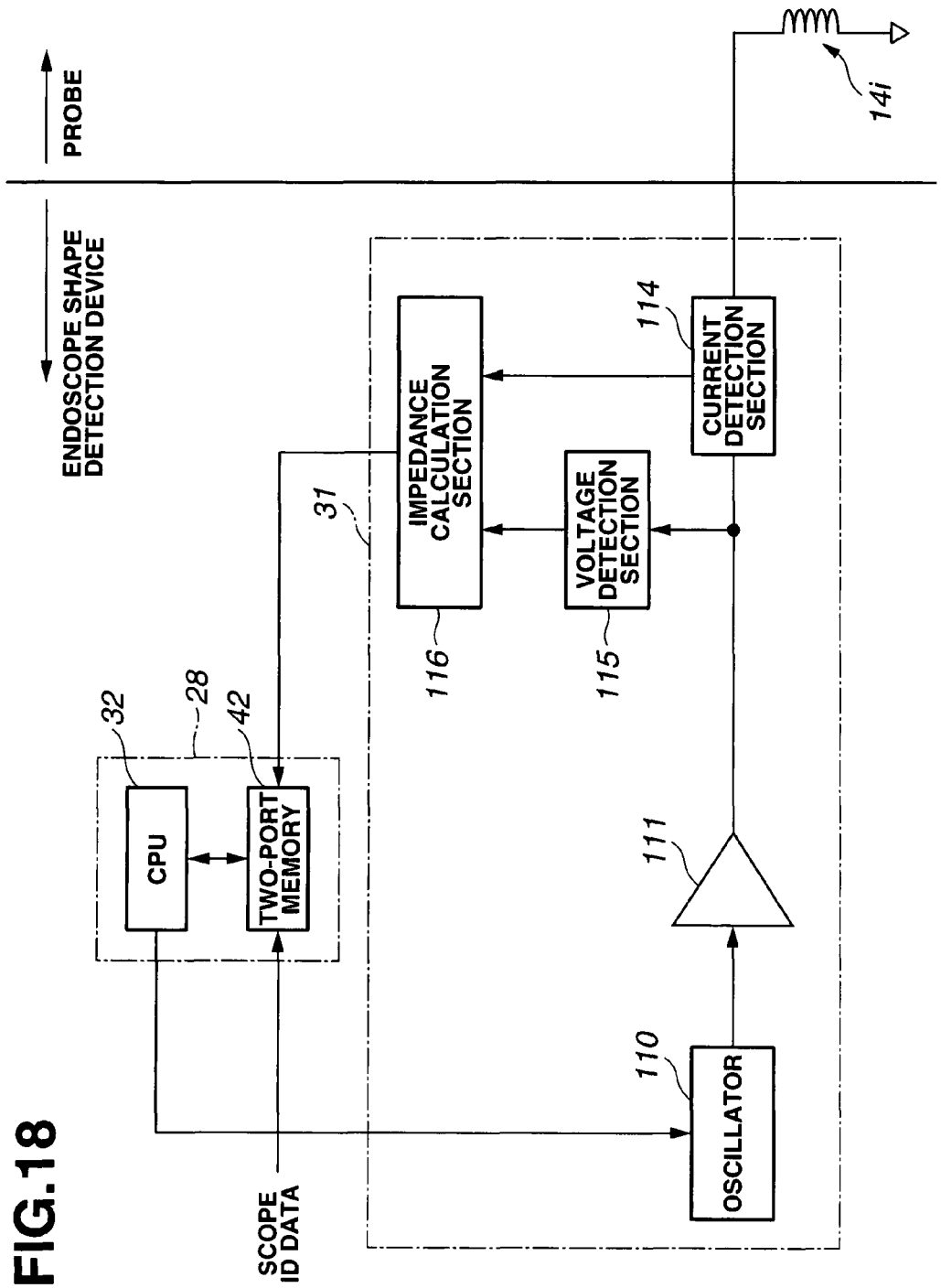
FIG. 18 is a view illustrating a source coil drive circuit section of an endoscope shape detection device according to a second embodiment of the present invention.
Figure 19:
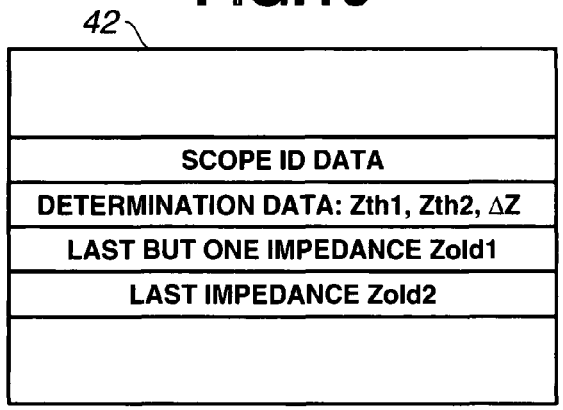
FIG. 19 is a view illustrating a memory map of a two-port memory according to the second embodiment.
Figure 20:
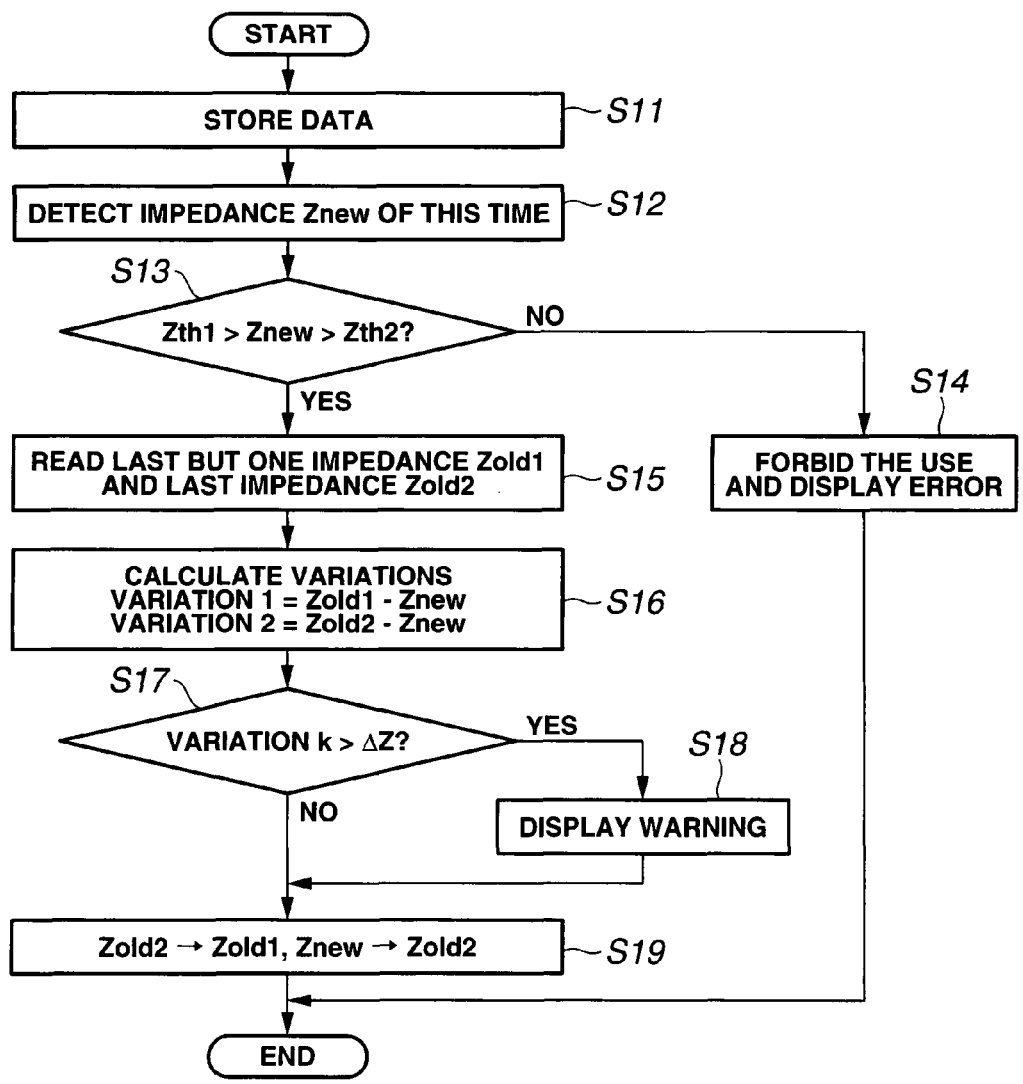
FIG. 20 is a flowchart illustrating an operation of an endoscope system according to the second embodiment.

FIGS. 18 to 20 relate to the second embodiment of the present invention.

FIG. 18 is a view illustrating a configuration of a source coil drive circuit section of an endoscope shape detection device, FIG. 19 is a view illustrating a memory map of a two-port memory, and FIG. 20 is a flowchart illustrating an operation of an endoscope system.

The second embodiment is similar to the first embodiment, and only differences will be described. The same reference numerals are given to similar configurations and their descriptions will be omitted.

In the present embodiment, as shown in FIG. 18, the source coil drive circuit section 31 of the endoscope shape detection device 3 includes a plurality of the oscillators 110, the amplifiers 111, current detection sections 114 that measure an alternate current running in the source coils 14i, voltage detection sections 115 that measure a volts alternating current being applied to the source coils 14i, and impedance calculation sections 116 that calculate an impedance Znew of the source coils 14i based on the measured alternate current and volts alternating current. The number of the elements above corresponds to the number of the source coils 14i.

The scope ID data and the various determination data of the nonvolatile memory 103 is taken into the endoscope shape detection device 3 through the video processor 10 when the endoscope system 1 is started up. As shown in FIG. 19, in the endoscope shape detection device 3, the scope ID data and the various determination data (Zth1, Zth2, $\Delta Z$) is stored on a predetermined address region of the two-port memory 42 via the control signal generation circuit section 40.

Other configurations are similar to those in the first embodiment. Now, thus configured endoscope shape detection process in the embodiment will be described.

When the endoscope system 1 is started up, the video processor 10 reads the scope ID data and the various determination data (Zth1, Zth2, $\Delta Z$) from the nonvolatile memory 103 of the electronic endoscope 6, and transmits the scope ID data and the various determination data (Zth1, Zth2, $\Delta Z$) to the endoscope shape detection device 3.

As shown in FIG. 20, at step S11, the CPU 32 of the endoscope shape detection device 3 stores the scope ID data and the various determination data (Zth1, Zth2, $\Delta Z$) on the predetermined address region of the two-port memory 42 through the control signal generation circuit section 40 (see FIG. 19).

Then, at step S12, the CPU 32 of the endoscope shape detection device 3 measures the alternate current running in the source coils 14i with the current detection section 114, and measures the volts alternating current being applied to the source coils 14i with the voltage detection section 115. Then, the CPU 32 calculates the impedance Znew of the source coils 14i based on the alternate current and the volts alternating current measured in the impedance calculation section 116.

The CPU 32 determines whether the impedance Znew detected at step S13 satisfies $|Zth1|<|Znew|<|Zth2|$ with respect to the determination data Zth1 and Zth2. In a case that it is determined that $|Zth1|<|Znew|<|Zth2|$ is not satisfied, the CPU 32 determines that the source coils 14i are broken or short-circuited, and then, at step S14, forbids the use of the probe 15, displays an error on the monitor 25, and finishes the process.

In a case that it is determined that $|Zth1|<|Znew|<|Zth2|$ is satisfied, at step S15, the CPU 32 reads a last but one detected impedance Zold1 and a last detected impedance Zold2 from the two-port memory 42. Then, at step S6, the CPU 32 calculates differences between the impedance Zold1 and the impedance Zold2 and the impedance Znew, that is, a variation $1=||Zold1|-|Znew||$, and a variation $2=||Zold2|-|Znew||$.

At step S17, the CPU 32 compares the variation 1 or the variation 2 to the determination data $\Delta Z$ to determine whether either variation $1>\Delta Z$ or variation $2>\Delta Z$ is satisfied. The variation 1 and the variation 2 indicate variation of impedance of the source coils 14i over time.

In a case that the CPU 32 determines either variation $1>\Delta Z$ or variation $2>\Delta Z$ is satisfied, it is considered that the source coils 14i are likely to break or short-circuit. Then, at step S18, the CPU 32 displays a warning for urging to replace the probe 15, or the like, on the monitor 25, and the process proceeds to step S19. In a case that both the variation 1 and variation 2 are within the $\Delta Z$, the process directly proceeds from step S17 to step S19.

At step S19, the CPU 32 rewrites the last but one impedance to the Zold2, and the last impedance to the Znew in the two-port memory 42, and finishes the process.

The above processes are time-sharingly performed with respect to all sixteen source coils 14i. Since the sixteen source coils 14i are time-sharingly magnetic-field driven at the time of shape detection, within the above processes, in the period that the sixteen source coils 14i are not magnetic-field driven, processes of steps S12 to S19 may be time-sharingly and continuously performed with respect to the all sixteen source coils 14i. Further, when the shape detection process is finished, the impedances Zold1 and Zold2 being stored finally on the two-port memory 42 may be stored on the nonvolatile memory 103 of the electronic endoscope 6 and the nonvolatile memory 103 may be rewritten.

As described above, in the present embodiment, similar advantages to those in the first embodiment can be obtained.

Third Embodiment

Figure 21:
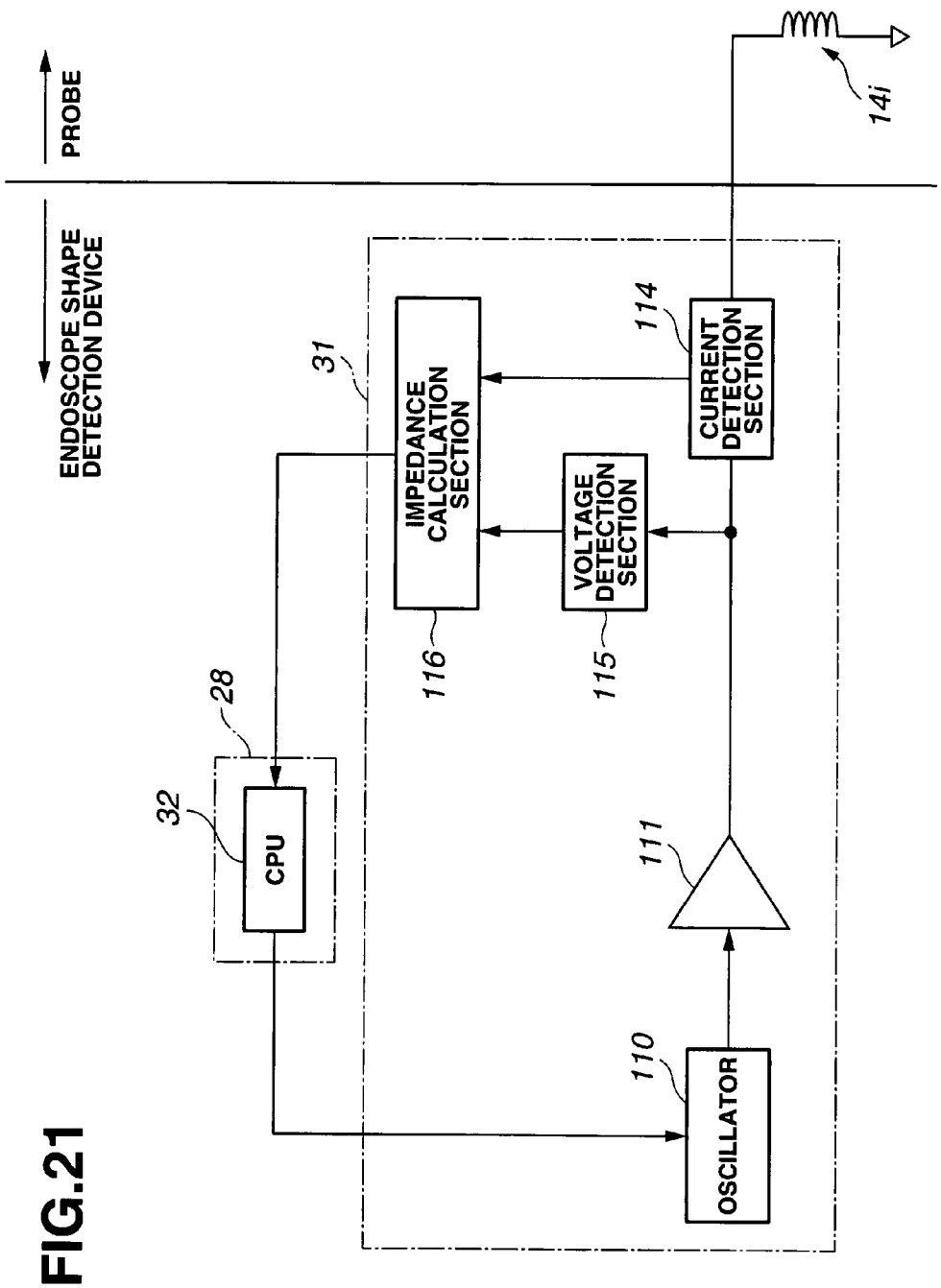
FIG. 21 is a view illustrating a source coil drive circuit section of an endoscope shape detection device according to a third embodiment of the present invention.
Figure 22:
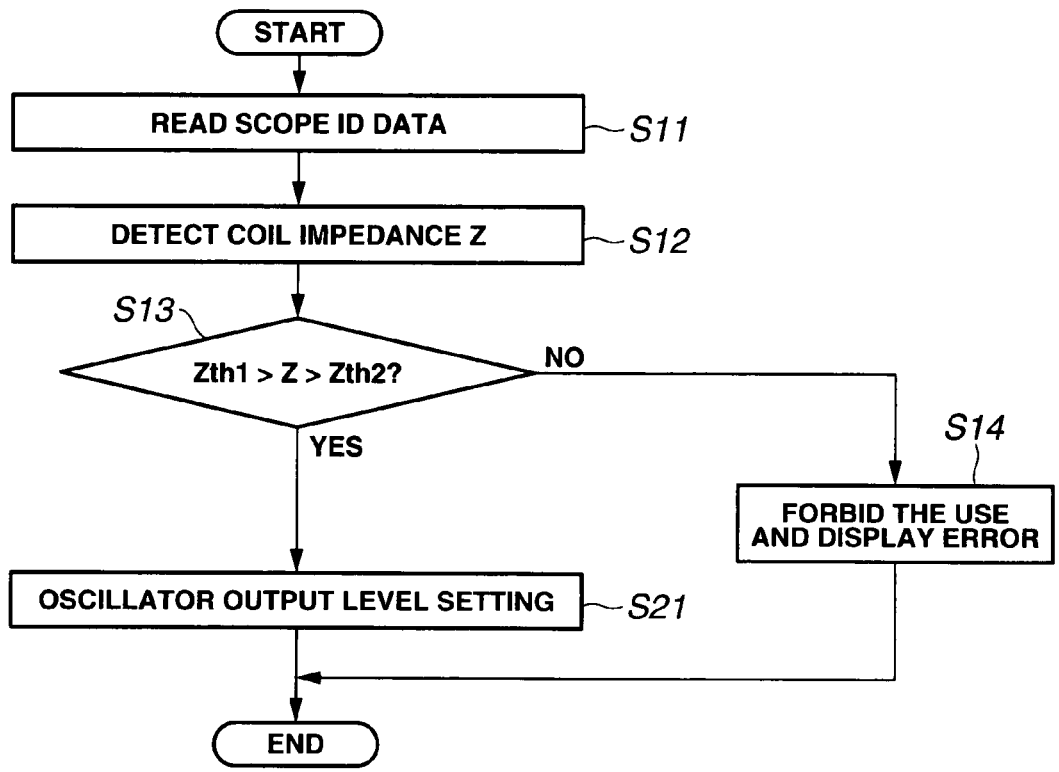
FIG. 22 is a flowchart illustrating an operation of an endoscope system according to the third embodiment.
Figure 23:
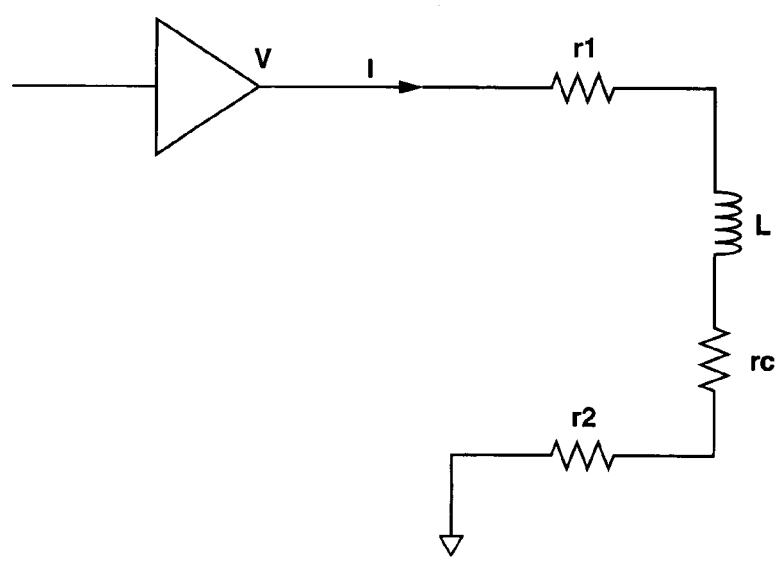
FIG. 23 is a view for explaining the process of the FIG. 22.
Figure 24:
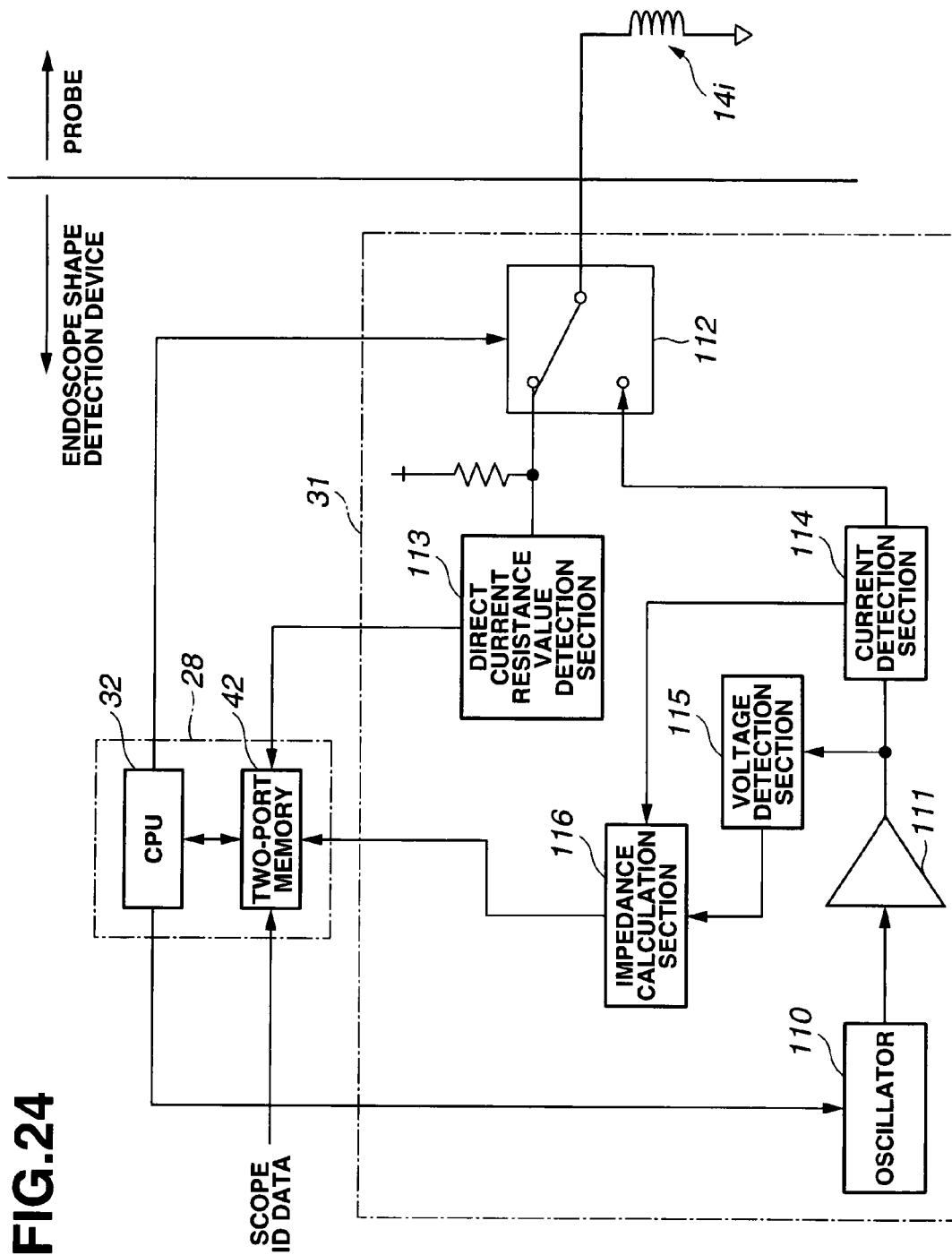
FIG. 24 is a view illustrating a modification of the source coil drive circuit section of FIG. 21.
Figure 25:
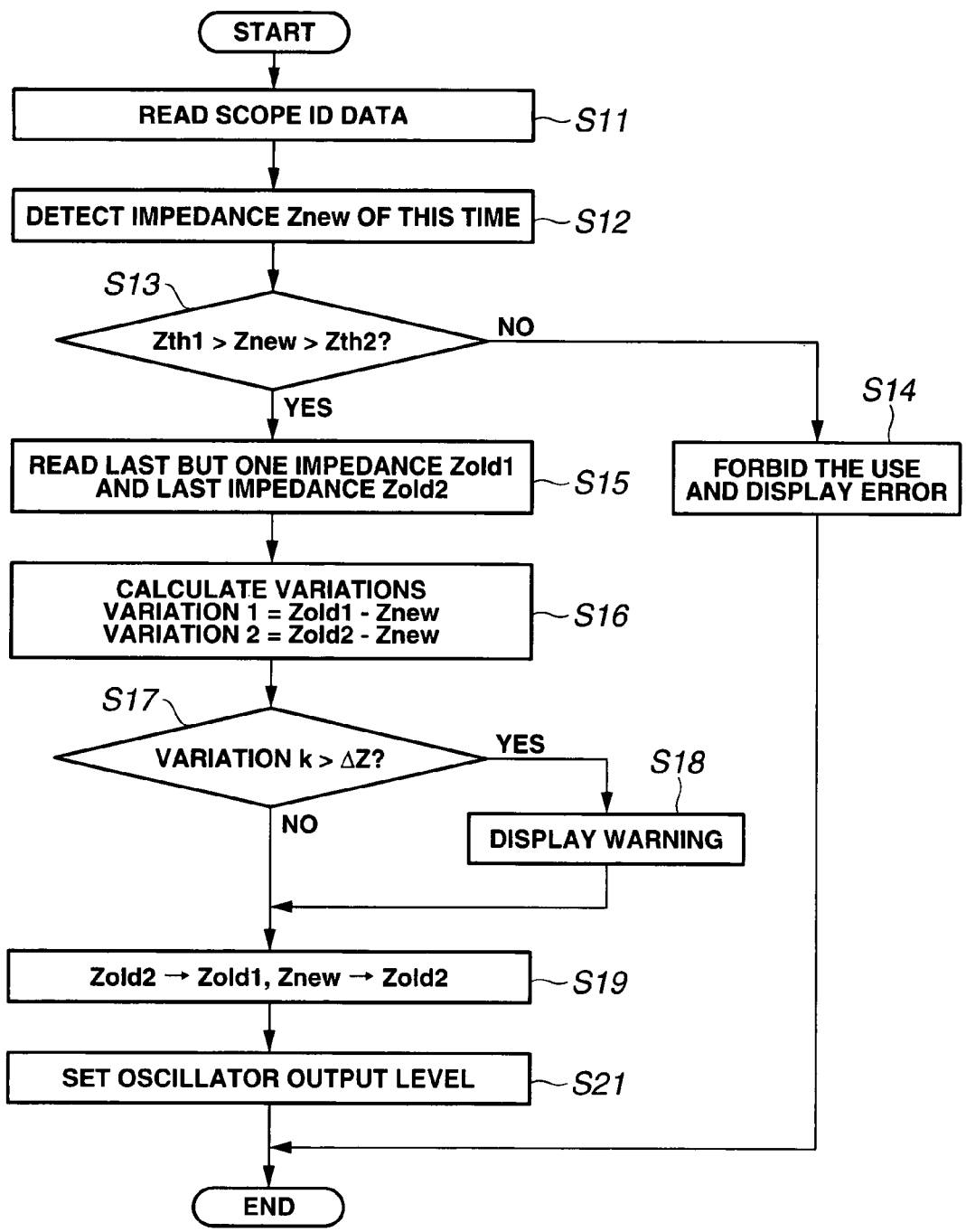
FIG. 25 is a view for explaining an operation of the source coil drive circuit section of FIG. 24.

FIGS. 21 to 25 relate to the third embodiment of the present invention. FIG. 21 is a view illustrating a configuration of a source coil drive circuit section of an endoscope shape detection device, FIG. 22 is a flowchart for explaining an operation of an endoscope system, FIG. 23 is a view for explaining the process of FIG. 22, FIG. 24 is a view illustrating a modification of the source coil drive circuit section of FIG. 21, and FIG. 25 is a view for explaining the operation of the source coil drive circuit section of FIG. 24.

The third embodiment is similar to the second embodiment, and only differences will be described. The same reference numerals are given to similar configurations and their descriptions will be omitted.

In the present embodiment, as shown in FIG. 21, the source coil drive circuit section is configured such that the CPU 32 controls an output voltage level of the oscillator 110 with the impedance Z of the source coils 14*i* calculated in the impedance calculation section 116. Other configurations are similar to those in the second embodiment.

Now, thus configured endoscope shape detection process in the present embodiment will be described.

As shown in FIG. 22, processes in steps 11 to 14 are similar to those in the second embodiment. When the processes in steps 11 to 14 are finished, at step S21, the CPU 32 controls the output voltage level of the oscillator 110 with the impedance Z of the source coils 14*i* calculated in the impedance calculation section 116. Other operations are similar to those in the second embodiment.

Now, the control of the output voltage level of the oscillator 110 with the impedance Z of the source coils 14*i* at step S21 will be described.

As an equivalent circuit of the source coils 14*i* shown in FIG. 23, if cable resistances of the probe 15 are r1, and r2, a direct current resistance of the source coils 14*i* is rc, an inductance of the source coils 14*i* is Lc, a current running in the source coils 14*i* is I, an output voltage of the amplifier 111 is V, an output frequency of the amplifier 111 is f, and R=r1+r2+rc, a magnetic field Φ generated from the source coils 14*i* and the impedance Z with respect to the amplifier 111 are defined as follows respectively.

$$\Phi = Lc \cdot I$$

$$|Z| = (R^2 + (2\pi f Lc)^2)^{1/2}$$

Since I=V/|Z|, the CPU 32 controls the output voltage level of the oscillator 110 based on |Z| to set V so that I becomes a predetermined current value, and then, a constant magnetic field output can be obtained without depending on R, that is, r1, r2, and rc.

As shown in FIG. 24, the source coil drive circuit section 31 of the endoscope shape detection device 3 may be configured by combining the first embodiment and the second embodiment so that the direct current resistance value and the impedance of the source coils 14*i* are detected respectively.

In the case of the configuration of FIG. 24, the direct current resistance R can be detected and the CPU 32 can calculate the inductance Lc using the impedance Z and the direct current resistance R. Accordingly, by controlling the output voltage level of the oscillator 110 to set V so that Φ=Lc·I=Lc·V/|V| comes to a predetermined value, a constant magnetic field output can be obtained.

With respect to the process in the case of the configuration of FIG. 24, as shown in FIG. 25, after processes in steps S11 to 19 in the second embodiment are performed, the process of step S21 may be performed.

As described above, in the present embodiment, based on the electric property of the coils, the source coil magnetic field can be controlled to be the constant magnetic field output.

Fourth Embodiment

Figure 26:
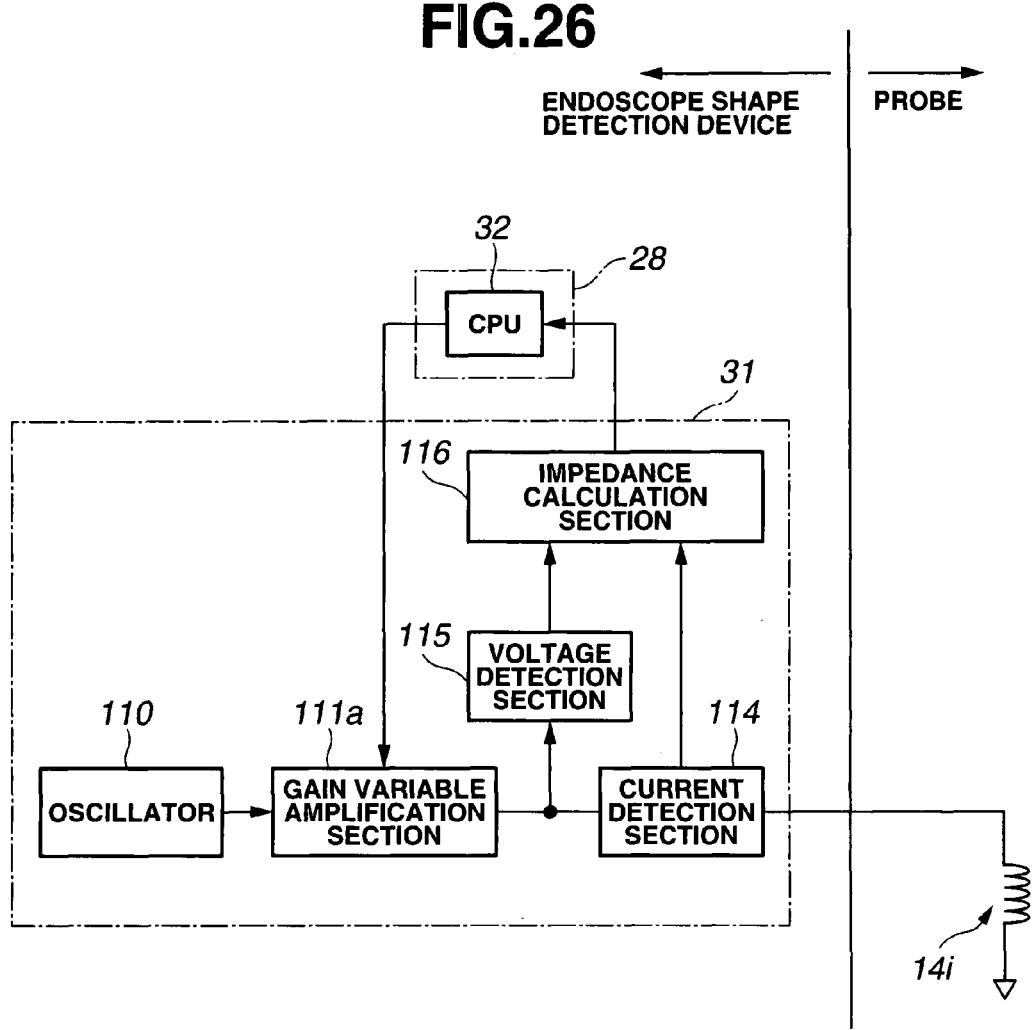
FIG. 26 is a view illustrating a configuration of a source coil drive circuit section of an endoscope shape detection device according to a fourth embodiment of the present invention.
Figure 27:
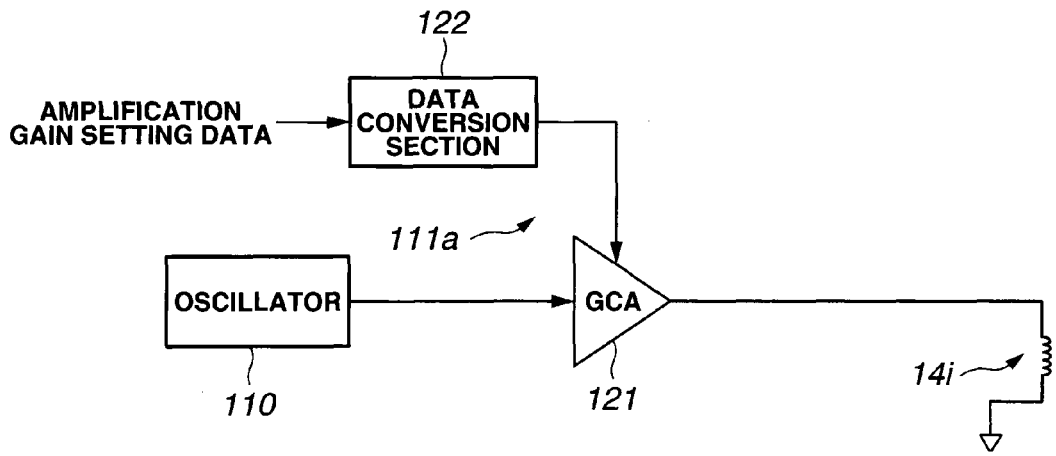
FIG. 27 is a view illustrating a configuration of the gain variable amplification section of FIG. 26.
Figure 28:
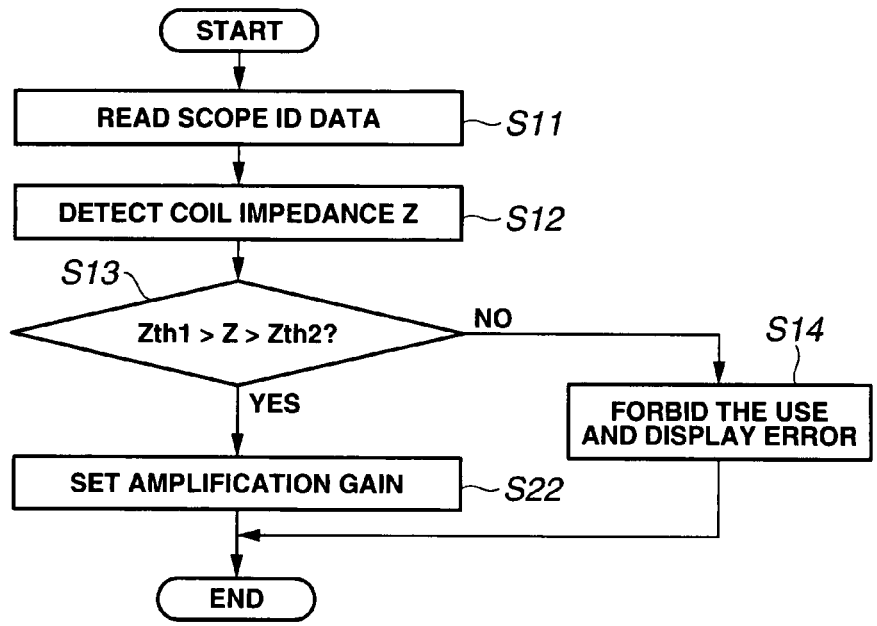
FIG. 28 is a flowchart for explaining an operation of the endoscope system according to the fourth embodiment.
Figure 29:
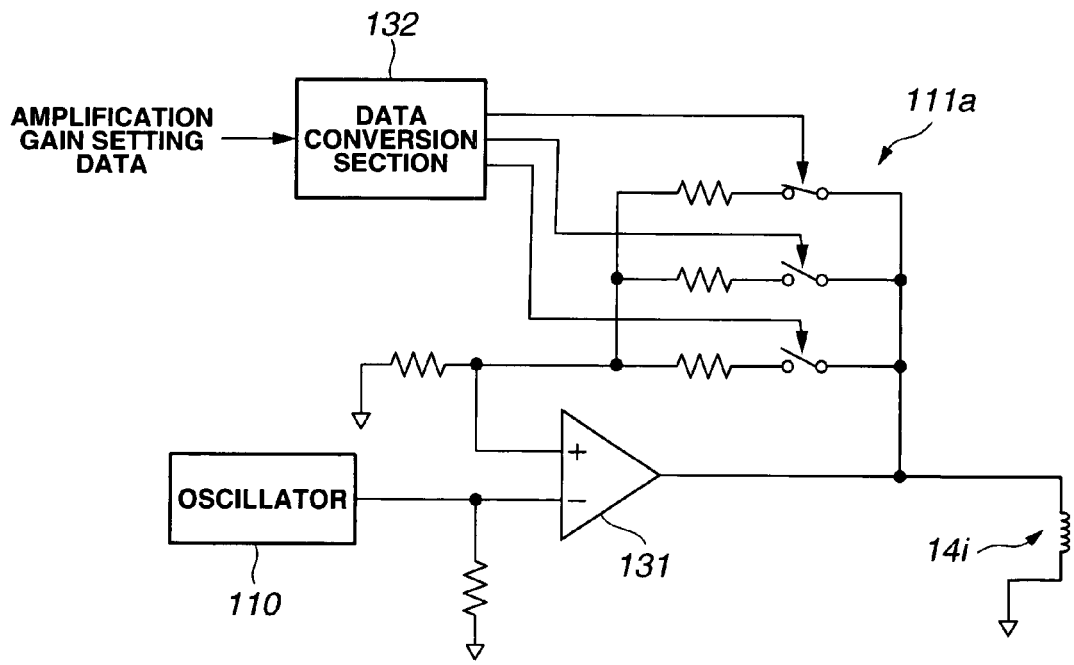
FIG. 29 is a view illustrating a configuration of a first modified example of the gain variable amplification section of FIG. 27.
Figure 30:
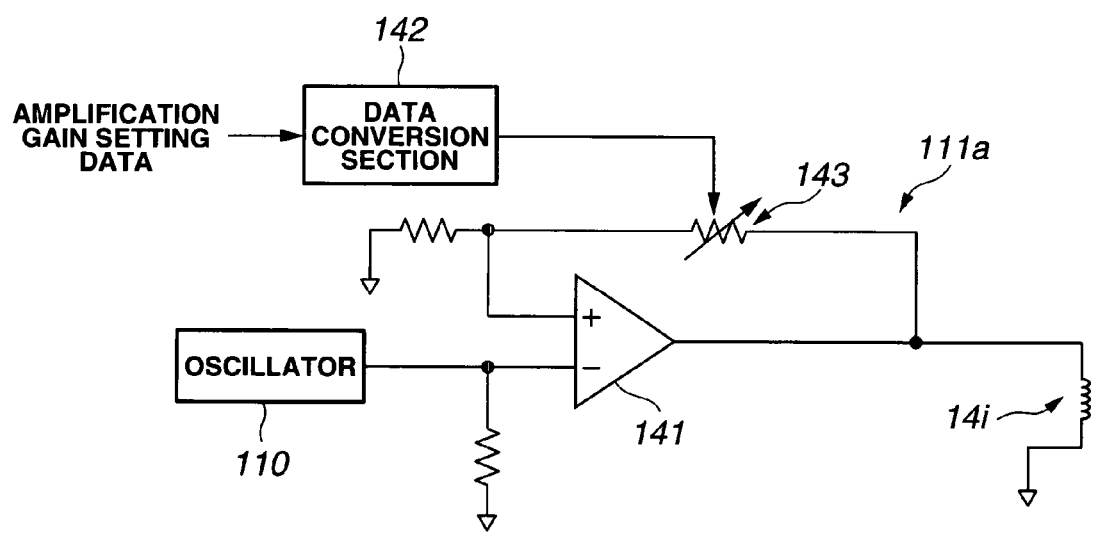
FIG. 30 is a view illustrating a configuration of a second modified example of the gain variable amplification section of FIG. 27.
Figure 31:
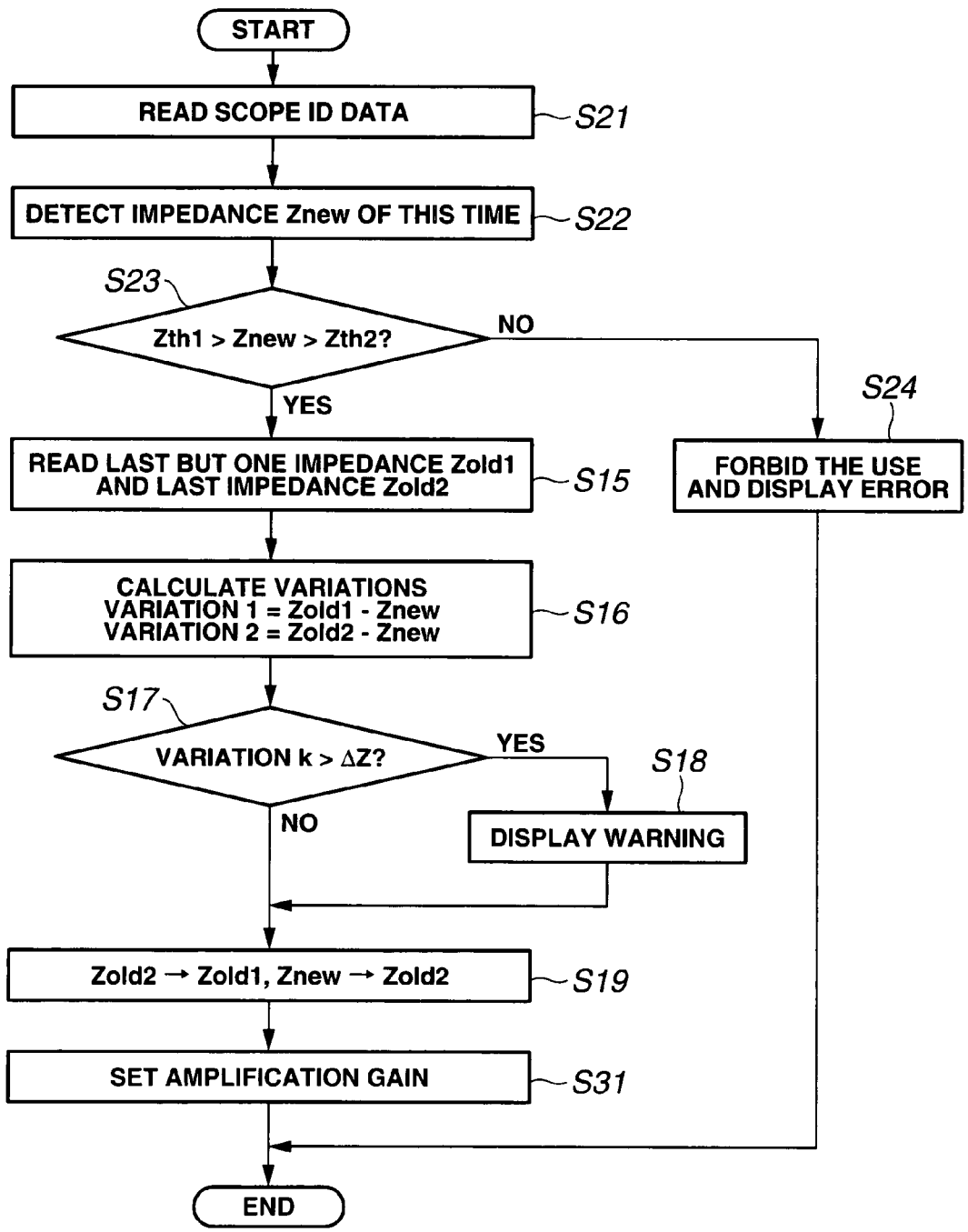
FIG. 31 is a flowchart of a modification of FIG. 28.
Figure 32:
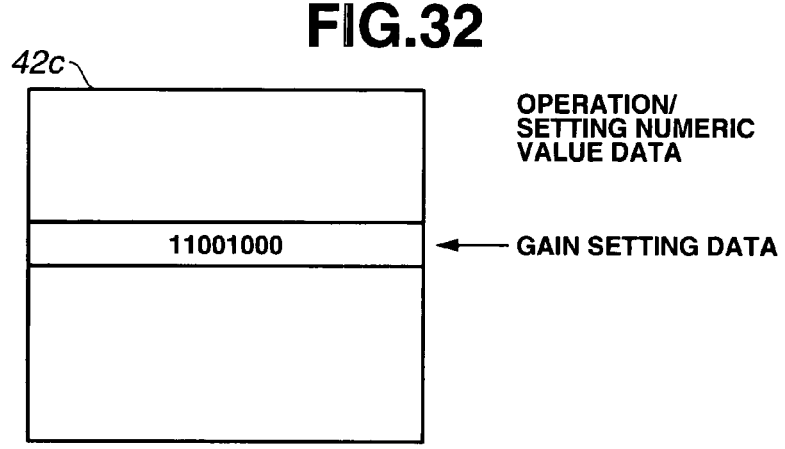
FIG. 32 is a view illustrating a memory map of a two-port memory according to the fourth embodiment.
Figure 33:
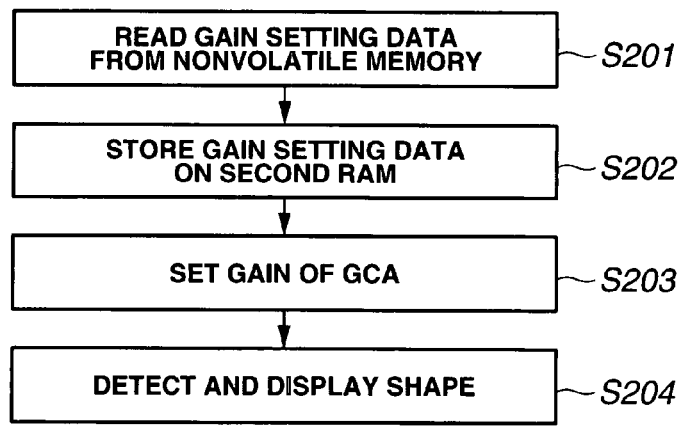
FIG. 33 is a flowchart illustrating an operation of a modified endoscope system according to the fourth embodiment.
Figure 34:
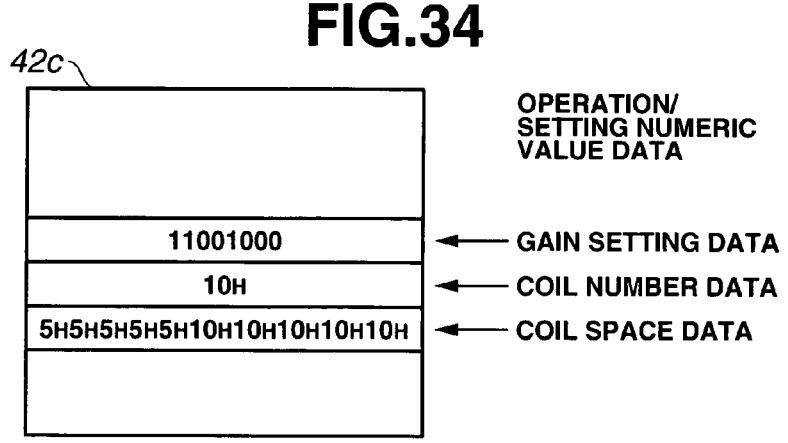
FIG. 34 is a view illustrating a memory map of a modified two-port memory according to the fourth embodiment.
Figure 35:
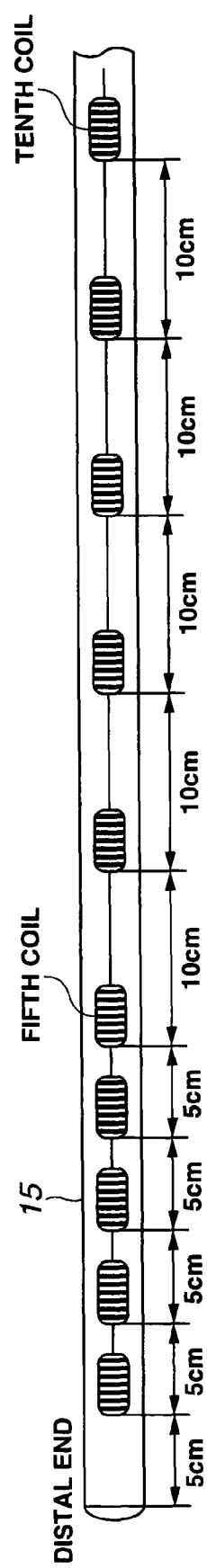
FIG. 35 is a view illustrating an example of modified data to be stored on the two-port memory according to the fourth embodiment.
Figure 36:
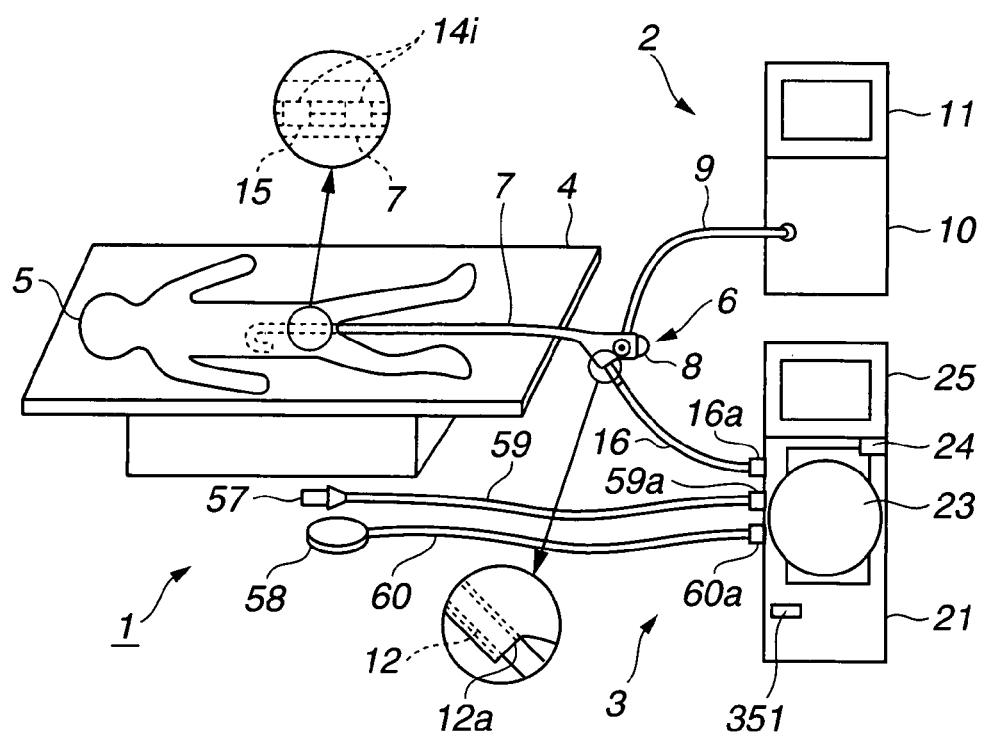
FIG. 36 is a view illustrating a modified endoscope system according to the fourth embodiment.

FIGS. 26 to 36 relate to the fourth embodiment of the present invention. FIG. 26 is a view illustrating a configuration of a source coil drive circuit section of an endoscope shape detection device, FIG. 27 is a view illustrating a configuration of the gain variable amplification section of FIG. 26, FIG. 28 is a flowchart for explaining an operation of an endoscope system, FIG. 29 is a view illustrating a configuration of a first modified example of the gain variable amplification section of FIG. 27, FIG. 30 is a view illustrating a configuration of a second modified example of the gain variable amplification section of FIG. 27, FIG. 31 is a flowchart of a modification of FIG. 28, FIG. 32 is a view illustrating a memory map of a two-port memory, FIG. 33 is a flowchart illustrating an operation of a modified endoscope system, FIG. 34 is a view illustrating a memory map of a modified two-port memory, FIG. 35 is a view illustrating an example of modified data to be stored on the two-port memory, and FIG. 36 is a view illustrating a modified endoscope system.

The fourth embodiment is similar to the third embodiment, and only differences will be described. The same reference numerals are given to similar configurations and their descriptions will be omitted.

In the present embodiment, as shown in FIG. 26, a gain variable amplification section 111*a* that varies a gain by a control of the CPU 32 is provided in place of the amplifier 111.

As shown in FIG. 27, the gain variable amplification section 111*a* includes a gain control amplifier (GCA) 121 that amplifies a sine wave from the oscillator 110 to generate (drive) an alternating magnetic field to a source coil and a data conversion section 122 that converts gain setting data (operation/setting numeric value data) into 8-bit serial data. A plurality of source coils 14*i* are driven by setting a gain of the GCA 121 according to the serial gain setting data from the data conversion section 122.

Other configurations are similar to those in the third embodiment.

Now, thus configured endoscope shape detection process in the present embodiment will be described.

As shown in FIG. 28, steps S11 to S14 are similar to those in the third embodiment. When the processes of steps S11 to S14 are finished, at step S22, the CPU 32 controls the gain of the GCA of the gain variable amplification section 111*a* based on the impedance Z of the source coils 14*i* calculated in the impedance calculation section 116 and finishes the process. Other operations are similar to those in the third embodiment.

In the embodiment, the gain of the GCA 121 is set using the gain setting data. However, it is not limited to the above, for example, as shown in FIG. 29, the gain variable amplification section 111*a* may include an operational amplifier 131 that switches a plurality of feedback resistances to set a gain and a data conversion section 132 that converts gain setting data into parallel data for setting a feedback resistance of the operational amplifier 131. Further, as shown in FIG. 30, the feedback resistance of the operational amplifier 131 may be formed by a digital potentiometer 141, and the gain variable amplification section 111*a* may include a data conversion section 142 that converts gain setting data into a control signal of the digital potentiometer 141.

The source coil drive circuit section 31 of the endoscope shape detection device 3 may be configured by combining the first embodiment and the second embodiment so that the direct current resistance value and the impedance of the source coils 14$i$ are detected respectively. In such a case, as shown in FIG. 31, after the processes of steps S11 to S19 are performed, the process of step S22 may be performed.

Incidentally, a device that detects an endoscope shape using magnetic fields and displays the detected endoscope shape is disclosed, for example, in Japanese Unexamined Patent Application Publication No. 2003-290129. The device drives a plurality of magnetic field generation elements disposed at predetermined intervals in an insertion section of an endoscope to be inserted into inside of a body to generate magnetic fields around the elements, detects three-dimensional positions of the each magnetic field generation element using magnetic field detection elements disposed outside the body, generates a curved line for serially connecting the each magnetic field generation element, and displays the three-dimensional image of the modeled insertion part with display means.

Operators, or the like can check a position, insertion shape, or the like of a tip part of the insertion part being inserted into the body by observing the image. Accordingly, the insertion operation to the target part or the like can be smoothly performed.

In the endoscope shape detection device of the above Japanese Unexamined Patent Application Publication No. 2003-290129, the sine wave is generated with the oscillator, the wave is amplified with the amplifier, the sine wave current is sent to the coil, and the alternating magnetic field is generated (driven). However, the gain of the amplifier is fixed, and if the type of the coil is changed, an appropriate drive is not performed.

That is, a thick endoscope uses a large coil and a thin endoscope uses a small coil, and further, a length of a lead wire or the like differs (if the insertion part of the endoscope has a great length and made of a thin material, the direct current resistance becomes high and not negligible at drive. As a result, if the type of the coil is changed, the impedance is changed. Then, for example, if the current is too large, the coil may be burned and cut, or, if the current is too weak, a only weak magnetic field may be generated.

Such a problem can be solved if the process step or data is changed depending on the coil to be used. However, because every time the endoscope to be used is changed, the type of the coil to be disposed differs, software or the data has to be frequently updated.

In the forth embodiment, without updating the software or the data, a shape detection or estimation can be simply performed with most suitable coil data. Hereinafter, detailed descriptions will be made with reference to FIGS. 32 to 36.

As shown in FIG. 7, in the operation part 8 of the base end side of the electronic endoscope 6, the nonvolatile memory 103 is provided. On the nonvolatile memory 103, in addition to the scope ID data for identifying the electronic endoscope 6 and various determination data for determining a state of the source coils 14$i$ that are provided in the probe 15, gain setting data, which is operation/setting numeric value data, of a drive signal used to drive the source coils 14$i$ disposed in the probe 15 is stored.

The gain setting data (operation/setting numeric value data) is taken in the endoscope shape detection device 3 through the video processor 10 on startup of the endoscope system 1. The endoscope shape detection device 3, as shown in FIG. 32, through the control signal generation circuit section (numeric value data write means) 40, stores the gain setting data (operation/setting numeric value data), for example, on a predetermined address region of the second RAM 42$c$ of the two-port memory 42 (see FIG. 4).

The source coil drive circuit section 31 of the endoscope shape detection device 3 includes the gain variable amplification section 111$a$ shown in FIG. 27. That is, the source coil drive circuit section 31 includes a plurality of the gain variable amplification sections 111$a$, as shown in FIG. 27, that include the oscillator 110 that generates a sine wave, the GCA 121 that amplifies the sine wave to generate (drive) an alternating magnetic field to a source coil and the data conversion section 122 that converts gain setting data (operation/setting numeric value data) into 8-bit serial data. A plurality of source coils 14$i$ are driven by setting a gain of the GCA 121 according to the serial gain setting data from the data conversion section 122.

The CPU 32 of the endoscope shape detection device 3, when the endoscope system 1 is started up, controls such that at step S201 the video processor 10 reads gain setting data (operation/setting numeric value data) from the nonvolatile memory 103 of the electronic endoscope 6 as shown in FIG. 33, and transmits the gain setting data (operation/setting numeric value data) to the endoscope shape detection device 3.

Then, at step S202, the CPU 32 of the endoscope shape detection device 3, through the control signal generation circuit section 40, stores the gain setting data (operation/setting numeric value data), on a predetermined address region of the second RAM 42$c$ of the two-port memory 42 (see FIG. 32).

For example, in a case that as a drive condition of the source coils of the probe 15 disposed in the electronic endoscope 6, the gain setting value of the GCA 121 is set to ⌈11001000⌋, the data ⌈11001000⌋ is stored on the nonvolatile memory 103 as the gain setting data (operation/setting numeric value data), and the data ⌈11001000⌋ is written on the predetermined address region of the second RAM 42$c$ of the two-port memory 42.

Then, on the predetermined address region, default gain setting data or gain setting data of the electronic endoscope 6 at the time the endoscope system 1 is previously used has been written. Accordingly, the CPU 32 performs a process to rewrite the data having been written on the predetermined address region, and stores the gain setting data (operation/setting numeric value data).

At step S203, the gain setting data (operation/setting numeric value data) is read from the predetermined address region of the second RAM 42$c$, and the data is outputted to the source coil drive circuit section 31 (see FIG. 27). Thus, in the source coil drive circuit section 31, the gain setting data (operation/setting numeric value data) is converted into serial gain setting data in the data conversion section 122, and the gain of the GCA 121 is set to a set value corresponding to the probe 15 to be disposed in the electronic endoscope 6.

Then, at step S204, the source coils 14$i$ are driven and an endoscope shape detection is performed. The detected endoscope shape is displayed on the liquid crystal monitor 25 and the process is finished.

As described above, the gain setting data that is the operation/setting numeric value data corresponding to the source coils of the probe 15 to be disposed in the electronic endoscope 6 is stored from the nonvolatile memory 103 of the electronic endoscope 6 onto the predetermined address region of the second RAM 42$c$ of the two-port memory 42 through the video processor 10, and the gain of the GCA 121 is directly set using the gain setting data. Accordingly, without updating the software or the data table for each of the probe 15 to be connected, the source coils can be readily driven on a most suitable drive condition.

In FIG. 27, in the source coil drive circuit section 31, the gain of the GCA 121 is set using the gain setting data. However, it is not limited to the above, the source coil drive circuit section 31 may be formed with, for example, the gain variable amplification section 111*a* shown in FIG. 29, or the gain variable amplifying section 111*a* shown in FIG. 30.

Further, with respect to the operation/setting numeric value data, the gain setting data has been described as an example. However, it is not limited to the above, for example, the number of source coils to be disposed in the probe 15 and the interval between the coils may be stored as the operation/setting numeric value data on the nonvolatile memory 103 of the electronic endoscope 6, and as shown in FIG. 34, on the predetermined address region of the second RAM 42*c* of the two-port memory 42, the data indicating the number of source coils and the interval may be written.

With respect to the types of the endoscopes, various types exist and some endoscopes have different insertion lengths. The number of coils used in endoscopes that have a long insertion section is large and the number of coils used in endoscopes that have a short insertion section is small. For example, in an endoscope shape detection device discussed in Japanese Unexamined Patent Application Publication No. 2000-93986, coils are arranged at narrow intervals in a bending section and at wide intervals in a flexible section.

Further, in an endoscope shape detection device discussed in Japanese Unexamined Patent Application Publication No. 2003-245242, when an endoscope shape is drawn, an interpolation process is performed to draw a smooth shape. The process requires a coil interval and the number of coils.

Further, some endoscope shape detection devices, for example, an endoscope shape detection device discussed in Japanese Unexamined Patent Application Publication No. 2001-231743 includes two bending sections.

In view of the above, on the nonvolatile memory 103 of the electronic endoscope 6, as shown in FIG. 35, for example, in a case that the number of coils is ten, coil intervals from an endoscope tip to a fifth coil are 5 cm, and coil intervals from the fifth coil to a tenth coil are 10 cm, coded data of [0, 5, 5, 5, 5, 5, 10, 10, 10, 10, 10] may be stored as the operation/setting numeric value data, and as shown in FIG. 34, on the predetermined address region of the second RAM 42*c* of the two-port memory 42, data indicating the number of source coils and the coil intervals may be written so that the endoscope shape detection device 3 draw a shape using the data.

In the above descriptions, the endoscope shape detection device 3 takes in the operation/setting numeric value data stored on the nonvolatile memory 103 of the electronic endoscope 6 through the video processor 10. However, it is not limited to the above, the endoscope shape detection device 3 may directly take in the operation/setting numeric value data stored on the nonvolatile memory 103 of the electronic endoscope 6.

Further, the operation/setting numeric value data stored on the nonvolatile memory 103 of the electronic endoscope 6 may be stored on a separate memory card (not shown) and when the electronic endoscope is used, as shown in FIG. 36, the memory card may be inserted into a slot 351 provided in the endoscope shape detection device, and the operation/setting numeric value data may be read. Then, the present invention can be applied to electronic endoscopes that do not have the nonvolatile memory 103, and without video processor 10, the operation/setting numeric value data can be taken in with the slot 351.

It is to be understood that the present invention is not limited to the above-described embodiments, various modifications, or changes can be made within the scope of the invention.

What is claimed is:

1. An endoscope shape detection device comprising:
a detection section having either one of a plurality of magnetic field generation elements and a plurality of magnetic field detection elements disposed in an insertion part of an endoscope to be inserted into a subject and the other elements disposed outside the subject, and, detecting each position of the one elements disposed in the insertion part using positions of the other elements as a reference;
a shape estimation section for estimating a shape of the endoscope insertion part based on the detection result of the detection section;
a property value detection section for detecting an electric property value of the magnetic field generation elements;
a storage section for storing a reference value of the electric property value; and
a state detection section for detecting a state of the magnetic field generation elements based on the electric property value of the magnetic field generation elements detected by the property value detection section and the reference value, wherein the storage section stores a past value of the electric property value of the magnetic field generation elements detected by the property value detection section as the reference value; and
the state detection section calculates a variation of the electric property value based on the past value of the electric property value stored on the storage section and a value of the electric property value of the present time detected by the property value detection section, and detects a state of the magnetic field generation elements based on the calculation result.

2. The endoscope shape detection device according to claim 1, wherein the state detection section compares the variation of the electric property value to a reference value of the variation, and based on the comparison result of the compared variation, detects a state of the magnetic field generation elements.

3. The endoscope shape detection device according to claim 2, wherein the state detection section calculates a variation of a first period based on a value at a first past time point of the electric property value and the value of the electric property value of the present time detected by the property value detection section, and calculates a variation of a second period based on a value at a second past time point of the electric property value and the value of the electric property value of the present time detected by the property value detection section.

4. The endoscope shape detection device according to claim 3, further comprising:
a notification control section for performing an information notification control for notifying a user of information based on the state of the magnetic field generation elements detected by the state detection section.

5. The endoscope shape detection device according to claim 4, further comprising:
a drive state control section for controlling a drive state of the magnetic field generation elements based on the state of the magnetic field generation elements detected by the state detection section.

6. The endoscope shape detection device according to claim 3, further comprising:
a drive state control section for controlling a drive state of the magnetic field generation elements based on the state of the magnetic field generation elements detected by the state detection section.

7. The endoscope shape detection device according to claim 6, wherein the drive state control section notifies variation over time of the magnetic field generation elements.

8. The endoscope shape detection device according to claim 2, further comprising:
a notification control section for performing an information notification control for notifying a user of information based on the state of the magnetic field generation elements detected by the state detection section.

9. The endoscope shape detection device according to claim 8, further comprising:
a drive state control section for controlling a drive state of the magnetic field generation elements based on the state of the magnetic field generation elements detected by the state detection section.

10. The endoscope shape detection device according to claim 2, further comprising:
a drive state control section for controlling a drive state of the magnetic field generation elements based on the state of the magnetic field generation elements detected by the state detection section.

11. The endoscope shape detection device according to claim 10, wherein the drive state control section notifies variation over time of the magnetic field generation elements.

12. The endoscope shape detection device according to claim 1, further comprising:
a notification control section for performing an information notification control for notifying a user of information based on the state of the magnetic field generation elements detected by the state detection section.

13. The endoscope shape detection device according to claim 12, further comprising:
a drive state control section for controlling a drive state of the magnetic field generation elements based on the state of the magnetic field generation elements detected by the state detection section.

14. The endoscope shape detection device according to claim 1, further comprising:
a notification control section for performing an information notification control for notifying a user of information based on the state of the magnetic field generation elements detected by the state detection section.

15. The endoscope shape detection device according to claim 14, further comprising:
a drive state control section for controlling a drive state of the magnetic field generation elements based on the state of the magnetic field generation elements detected by the state detection section.

16. The endoscope shape detection device according to claim 1, further comprising:
a drive state control section for controlling a drive state of the magnetic field generation elements based on the state of the magnetic field generation elements detected by the state detection section.

17. The endoscope shape detection device according to claim 16, wherein the drive state control section notifies variation over time of the magnetic field generation elements.

18. The endoscope shape detection device according to claim 1, further comprising:
a drive state control section for controlling a drive state of the magnetic field generation elements based on the state of the magnetic field generation elements detected by the state detection section.

19. The endoscope shape detection device according to claim 18, wherein the drive state control section notifies variation over time of the magnetic field generation elements.

20. An endoscope shape detection device including a detection section having either one of a plurality of magnetic field generation elements and a plurality of magnetic field detection elements disposed in an insertion part of an endoscope to be inserted into a subject and the other elements disposed outside the subject, and, detecting each position of the one elements disposed in the insertion part using positions of the other elements as a reference, and a shape estimation section for controlling the detection section and estimating a shape of the endoscope insertion part based on the detection result of the detection section, the device comprising: a property value detection section for detecting an electric property value of the magnetic field generation elements; and
a drive state control section for controlling a drive state of the magnetic field generation elements based on the electric property value, wherein the drive state control section controls a drive voltage of the magnetic field generation elements based on the electric property value.

21. The endoscope shape detection device according to claim 20, wherein the drive state control section notifies variation over time of the magnetic field generation elements.

22. The endoscope shape detection device according to claim 21, wherein the electric property value is a direct current resistance value of the magnetic field generation elements.

23. The endoscope shape detection device according to claim 21, wherein the electric property value is an impedance value of the magnetic field generation elements.

24. The endoscope shape detection device according to claim 20, wherein the electric property value is a direct current resistance value of the magnetic field generation elements.

25. The endoscope shape detection device according to claim 20, wherein the electric property value is an impedance value of the magnetic field generation elements.

26. The endoscope shape detection device according to claim 20, wherein the electric property value is an impedance value of the magnetic field detection elements.

27. The endoscope shape detection device according to claim 20, wherein the electric property value is an impedance value and a direct current resistance value of the magnetic field detection elements.

* * * * *